(12) United States Patent
Paolino et al.

(10) Patent No.: US 9,433,454 B2
(45) Date of Patent: Sep. 6, 2016

(54) VARIABLE ANGLE SCREWS, PLATES AND SYSTEMS

(71) Applicant: AMEI TECHNOLOGIES, INC., Wilmington, DE (US)

(72) Inventors: John Paolino, Bedminster, NJ (US); John Lovell, North Bergen, NJ (US); Guy F. Birkenmeier, Dallas, TX (US)

(73) Assignee: AMEI TECHNOLOGIES, INC., Wilmington, DE (US)

( * ) Notice: Subject to any disclaimer, the term of this patent is extended or adjusted under 35 U.S.C. 154(b) by 404 days.

(21) Appl. No.: 13/830,387

(22) Filed: Mar. 14, 2013

(65) Prior Publication Data
US 2014/0277180 A1    Sep. 18, 2014

(51) Int. Cl.
*A61B 17/80* (2006.01)
*A61B 17/86* (2006.01)

(52) U.S. Cl.
CPC ....... *A61B 17/8057* (2013.01); *A61B 17/8605* (2013.01); *Y10T 408/03* (2015.01)

(58) Field of Classification Search
CPC ............ A61B 17/864; A61B 17/8014; A61B 17/8052; A61B 17/8057; A61B 17/86
USPC ....... 606/300, 301, 305, 308, 309, 310, 311, 606/315, 316, 317; 411/412, 413, 417, 418
See application file for complete search history.

(56) References Cited

U.S. PATENT DOCUMENTS

| | | | |
|---|---|---|---|
| 2,816,302 A | 12/1957 | Bauer | |
| 3,504,722 A * | 4/1970 | Breed | B21H 3/025 411/168 |
| 3,741,205 A | 6/1973 | Markolf et al. | |
| 3,842,877 A | 10/1974 | Andrews | |
| 4,010,671 A | 3/1977 | Hubbard et al. | |
| 4,067,256 A | 1/1978 | Turner | |
| 4,637,767 A | 1/1987 | Yaotani et al. | |
| 4,713,004 A | 12/1987 | Linkow et al. | |
| 4,755,092 A | 7/1988 | Yaniv | |
| 4,789,288 A | 12/1988 | Peterson | |
| 4,867,144 A | 9/1989 | Karas et al. | |
| 4,907,930 A | 3/1990 | Peterson | |
| 4,927,302 A | 5/1990 | Beaty | |
| 4,973,209 A | 11/1990 | Essom et al. | |
| 4,993,575 A | 2/1991 | Maes | |
| 5,102,336 A | 4/1992 | Linkow | |
| 5,129,899 A | 7/1992 | Small et al. | |
| 5,326,208 A | 7/1994 | Werner | |

(Continued)

FOREIGN PATENT DOCUMENTS

| | | |
|---|---|---|
| EP | 0403322 A1 | 12/1990 |
| EP | 1087149 B2 | 3/2001 |

(Continued)

OTHER PUBLICATIONS eBay, 140 pcs NAS679A5 Self-Locking Nut 5/16-24 Thread, 2013, 2 pages.

(Continued)

*Primary Examiner* — Anu Ramana
(74) *Attorney, Agent, or Firm* — Baker & McKenzie LLP

(57) ABSTRACT

The present disclosure relates, according to some embodiments, to orthopedic implantable device technology, and more specifically to variable angle implantable devices, systems, and methods.

27 Claims, 19 Drawing Sheets

(56) References Cited

U.S. PATENT DOCUMENTS

| | | | |
|---|---|---|---|
| 5,340,254 A * | 8/1994 | Hertel | F16B 25/0021 411/311 |
| 5,486,176 A | 1/1996 | Hildebrand et al. | |
| 5,490,746 A | 2/1996 | Baker | |
| 5,544,993 A * | 8/1996 | Harle | B23G 5/04 411/411 |
| 5,603,266 A | 2/1997 | Nash | |
| 5,637,817 A | 6/1997 | Sherman | |
| 5,951,224 A | 9/1999 | DiStasio | |
| 6,158,938 A | 12/2000 | Savoji | |
| 6,221,073 B1 | 4/2001 | Weiss et al. | |
| 6,358,250 B1 | 3/2002 | Orbay | |
| 6,364,882 B1 | 4/2002 | Orbay | |
| 6,439,818 B1 | 8/2002 | Nagayama | |
| 6,440,135 B2 | 8/2002 | Orbay et al. | |
| 6,454,769 B2 | 9/2002 | Wagner et al. | |
| 6,468,014 B2 | 10/2002 | Chen | |
| 6,474,918 B1 | 11/2002 | Kelch | |
| D469,875 S | 2/2003 | Bryant et al. | |
| 6,540,619 B2 | 4/2003 | Kato | |
| 6,547,790 B2 | 4/2003 | Harkey, III et al. | |
| 6,592,586 B1 | 7/2003 | Michelson | |
| 6,706,046 B2 | 3/2004 | Orbay et al. | |
| 6,722,833 B2 | 4/2004 | Birkelbach | |
| 6,730,090 B2 | 5/2004 | Orbay et al. | |
| 6,866,665 B2 | 3/2005 | Orbay | |
| 6,936,050 B2 | 8/2005 | Michelson | |
| 6,955,677 B2 | 10/2005 | Dahners | |
| D520,637 S | 5/2006 | Kay et al. | |
| 7,041,105 B2 | 5/2006 | Michelson | |
| D536,453 S | 2/2007 | Young et al. | |
| 7,179,036 B2 | 2/2007 | Griffin et al. | |
| 7,186,256 B2 | 3/2007 | Michelson | |
| 7,399,301 B2 | 7/2008 | Michelson | |
| 7,491,220 B2 | 2/2009 | Coughlin | |
| D589,149 S | 3/2009 | Strnad et al. | |
| 7,572,282 B2 | 8/2009 | Boomer et al. | |
| 7,607,854 B1 | 10/2009 | Goodson et al. | |
| 7,637,928 B2 | 12/2009 | Fernandez | |
| 7,695,472 B2 | 4/2010 | Young | |
| 7,704,250 B2 | 4/2010 | Michelson | |
| 7,740,630 B2 | 6/2010 | Michelson | |
| 7,771,457 B2 | 8/2010 | Kay et al. | |
| D623,744 S | 9/2010 | Strnad et al. | |
| 7,799,061 B2 | 9/2010 | Kay et al. | |
| 7,803,157 B2 | 9/2010 | Michelson | |
| 7,811,285 B2 | 10/2010 | Michelson | |
| 7,833,226 B2 | 11/2010 | Grabowski et al. | |
| 7,951,176 B2 | 5/2011 | Grady, Jr. et al. | |
| 7,955,364 B2 * | 6/2011 | Ziolo | A61B 17/8057 606/291 |
| 7,963,980 B1 | 6/2011 | Freeman et al. | |
| D646,785 S | 10/2011 | Milford | |
| 8,043,346 B2 | 10/2011 | Markworth | |
| D648,027 S | 11/2011 | Vancelette et al. | |
| 8,057,520 B2 | 11/2011 | Duchame et al. | |
| 8,216,285 B2 | 7/2012 | Markworth | |
| 8,231,663 B2 | 7/2012 | Kay et al. | |
| 8,246,661 B2 | 8/2012 | Beutter et al. | |
| 8,246,664 B2 | 8/2012 | Terrill et al. | |
| 8,257,403 B2 | 9/2012 | Den Hartog et al. | |
| 8,486,116 B2 | 7/2013 | Heilman | |
| 8,617,223 B2 | 12/2013 | Matityahu | |
| 2002/0045901 A1 | 4/2002 | Wagner et al. | |
| 2002/0183752 A1 | 12/2002 | Steiner et al. | |
| 2005/0131413 A1 * | 6/2005 | O'Driscoll | A61B 17/8052 606/286 |
| 2006/0009771 A1 | 1/2006 | Orbay et al. | |
| 2006/0025772 A1 | 2/2006 | Leibel et al. | |
| 2007/0073298 A1 | 3/2007 | Beutter et al. | |
| 2007/0162019 A1 | 7/2007 | Burns et al. | |
| 2008/0091198 A1 | 4/2008 | Liebel et al. | |
| 2008/0234749 A1 | 9/2008 | Forstein | |
| 2009/0318921 A1 | 12/2009 | White et al. | |
| 2011/0190827 A1 | 8/2011 | Konieczynski et al. | |
| 2011/0224737 A1 | 9/2011 | Lewis et al. | |
| 2012/0158058 A1 | 6/2012 | Michelson | |
| 2012/0265202 A1 | 10/2012 | Schwammberger et al. | |
| 2014/0018862 A1 * | 1/2014 | Koay | A61B 17/8057 606/281 |

FOREIGN PATENT DOCUMENTS

| | | |
|---|---|---|
| EP | 1635077 B1 | 8/2007 |
| WO | 9719862 A1 | 6/1997 |
| WO | 0063566 A1 | 10/2000 |
| WO | 0144672 A1 | 6/2001 |
| WO | 2004084701 A2 | 10/2004 |
| WO | 2011/085272 A1 | 7/2011 |

OTHER PUBLICATIONS

Von Strempl, et al., "The stability of bone screws in the os sacrum," Eur Spine J (1998), vol. 7, pp. 313-320.

Richter, et al., "Biomechanical evaluation of a new modular rod-screw implant system for posterior instrumentation of the occipito-cervical spine: in-vitro comparison with two established implant systems," Eur Spine J (2000), vol. 9, pp. 417-425.

Ulrich, et al., "Internal fixation on the lower cervical spine—biomechanics and clinical practice of procedures and implants," Eur Spine J (2001), vol. 10, pp. 88-100.

Barnes, et al., "Early results using the Atlantis anterior cervical plate system," Neurosurg Focus 12 (1), Articles 13, 2002, 7 pages.

ATLAS: Fasteners for Construction, "FastenerTalk: Metal Building Systems Information, 18-8 Stainless Steel Self-Tapping Sheeting Screws," No. 101, Atlas Bolt & Screw Company, Ashland, Ohio, downloaded 2013 from http://www.atlasfasteners.com/images/FastenerTalk-101.pdf, 2 pages.

Fastener Training Institute, Table of Contents, retrieved 2013, 24 pages.

Arnold, et al., "Efficacy of variable-angle screws in transpedicular fixation," Neurosurg Focus 7 (6), Article 1, 1999, 11 pages.

Pem, "The Self-Clinching Fastener Handbook," accessed Apr. 12, 2013, http://www.pemnet.com/fastening_products/pdf/Handbook.pdf, 16 pages.

Sukhtian, et al., "An external fixation device: preliminary communication," Journal of the Royal Society of Medicine, vol. 72, Nov. 1979, 4 pages.

Omeis, et al., "History of instrumentation for stabilization of the subaxial cervical spine," Neurosurg Focus 16 (1), Article 10, 2004, 6 pages.

ParkTool Co., "Repair Help and Education," ParkTool Blog, Basic Thread Concepts, http://www.parktook.com/blog/repair-help/basic-thread-concepts, accessed Apr. 11, 2013, 9 pages.

TineLok, "English Specifications," http://www.tinelok/com/Catalog/bolt_quote.pdf, accessed Apr. 11, 2013, 3 pages.

Resnick, "Anterior cervicothoracic junction corpectomy and plate fixation without sternotomy," Neurosurg Focus 12 (1), Article 7, 2002, 6 pages.

Baldwin, et al, Sacral fixation using iliac instrumentation and a variable-angle screw device, J Neurosurg, vol. 81, pp. 313-316, 1994, 4 pages.

Shuter, et al., USGS, Department of the Interior, "Techniques of Water-Resource Investigations of the United States Geological Survey, Chapter F1, Application of Drilling, Coring and Sampling Techniques to Test Holes and Wells," 1989, 36 pages.

International Search Report and Written Opinion, PCT/US2014/025952, dated Sep. 19, 2014, 22 page.

* cited by examiner

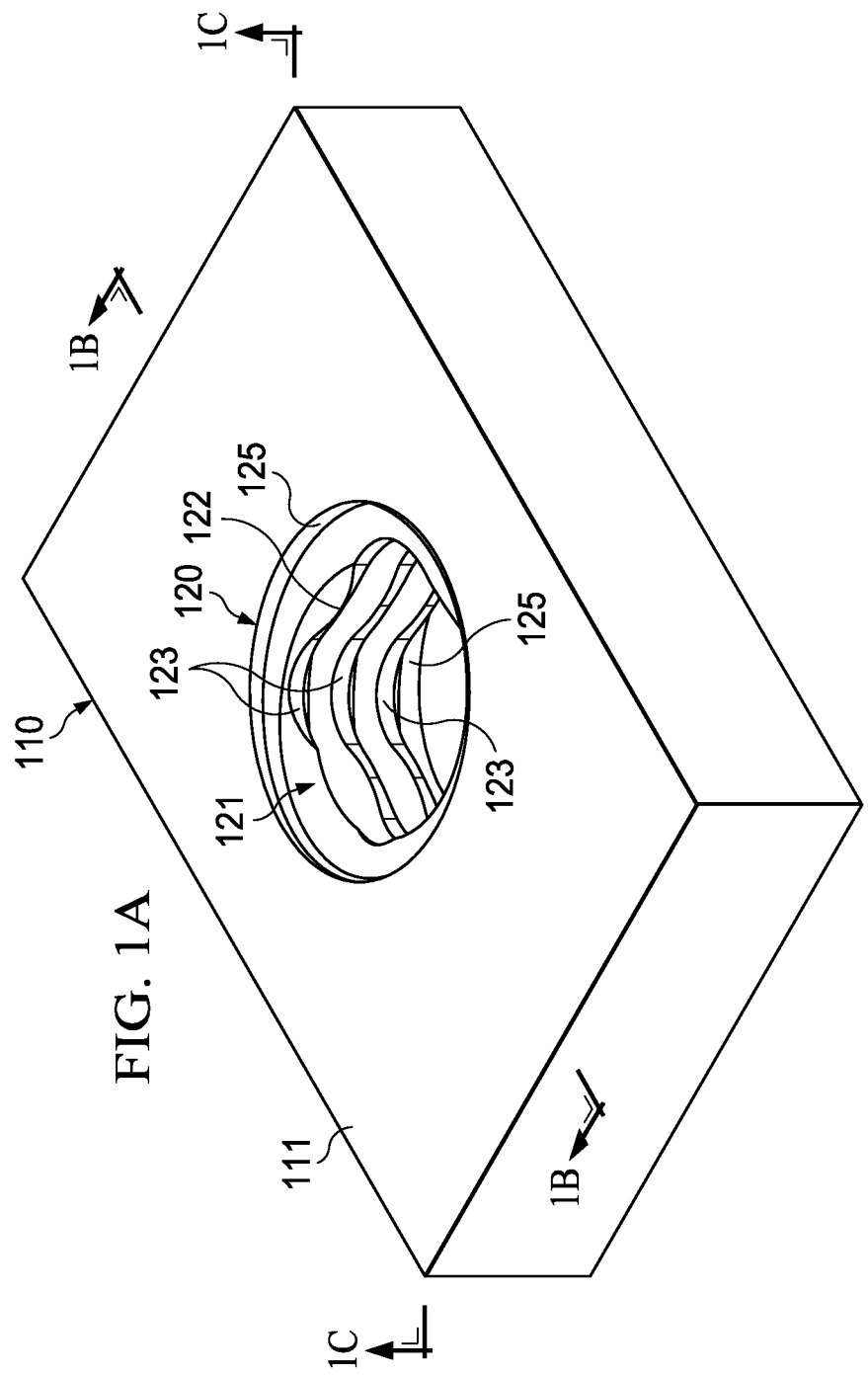

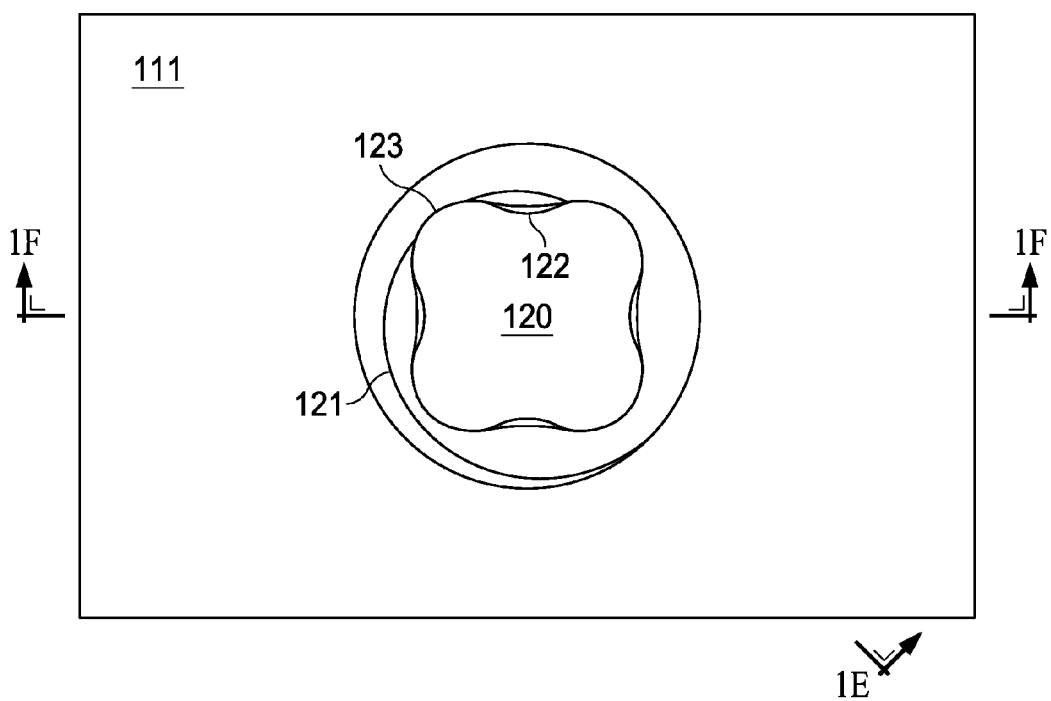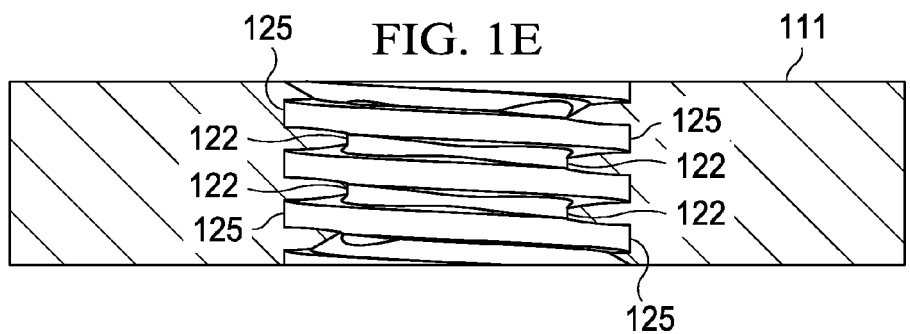

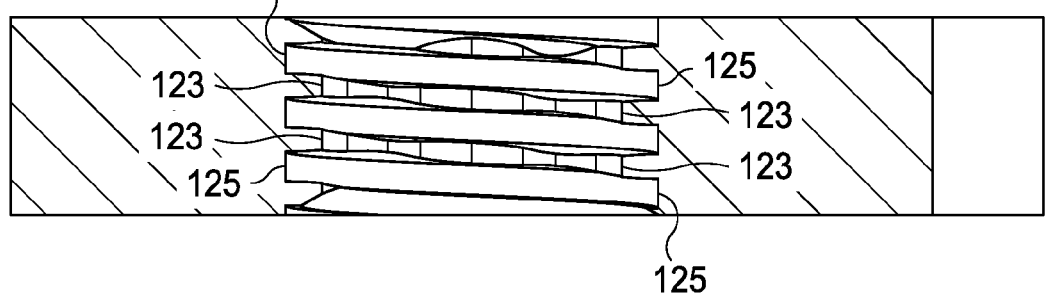
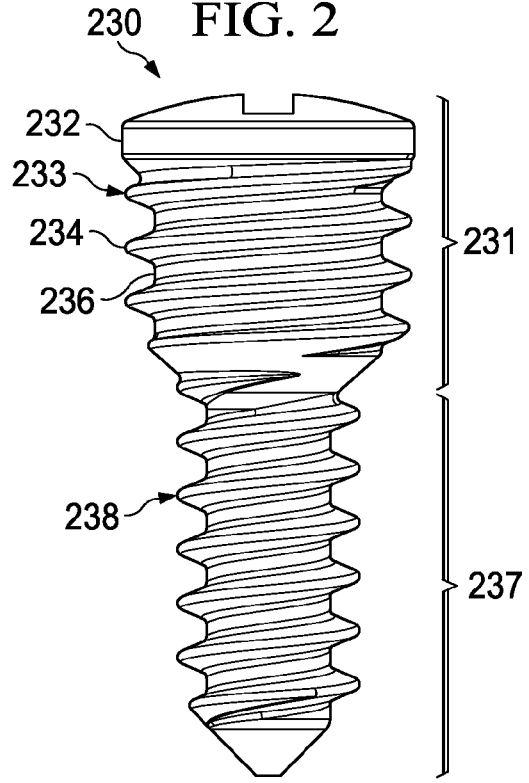

VARIABLE ANGLE SCREWS, PLATES AND SYSTEMS

FIELD OF THE DISCLOSURE

The present disclosure relates, in some embodiments, to orthopedic implantable device technology, and more specifically to variable angle implantable devices, systems, and methods.

BACKGROUND

Bone plates and screws may be used to stabilize bones in the body of a subject (e.g., human, non-human animal). Plates may be secured to bones using screws that are directed inwardly through holes in the plates and into underlying bone. While a screw may be inserted with its longitudinal axis aligned with the axis of the hole through which it passes, this angle may not be optimal in all circumstances. For example, an alternate insertion angle may be desired in light of the shape of the underlying bone, the forces to which it is subjected, and/or the nature of the condition to be stabilized.

SUMMARY

Accordingly, a need has arisen for improved bone fixation devices and systems that permit practitioners to select the angle at which the fixation member is inserted. The present disclosure relates, in some embodiments, to orthopedic implantable device technology, and more specifically to variable and/or selectable angle implantable devices, systems, and methods. A fixation member angle may be assessed with respect to a reference point on the fixation member (e.g., a longitudinal axis) and a reference point on a subject's bone, an associated plate, and/or a longitudinal axis of a hole through which the fixation member is inserted.

The present disclosure relates, according to some embodiments, to a variable angle orthopedic plate. For example, a plate may comprise an upper surface, a bone facing surface, and/or at least one variable angle through hole between the upper surface and the bone facing surface. In some embodiments, a through hole may have a generally cylindrical shape with a central hole axis and/or may comprise a single continuous thread, the apex of which defines a central hole aperture of radius ($r_{aperture}$). A hole may comprise a thread trough defining a total hole radius of ($r_{hole}$), according to some embodiments. A thread may have, in some embodiments, at least one indentation along its length, each indentation having a radius ($r_{indent}$), wherein $r_{aperture} < r_{indent} < r_{hole}$. A variable angle hole may be operable to engage a threaded head of an orthopedic fastener at a first angle aligned with the central hole axis and at least one other angle (e.g., $0 < \alpha \leq 60°$. A thread may comprise a plurality of indentations arranged in at least one column parallel or substantially parallel to the central hole axis. For example, a thread may comprise a plurality of indentations arranged in 2 columns, 3 columns, 4 columns, 5 columns, or 6 columns, each parallel or substantially parallel to the central hole axis and spaced around (e.g., uniformly spaced around) the central hole axis. A thread, in some embodiments, may span the length of the hole from the upper surface to the bone facing surface. According to some embodiments, a thread may further comprise one or more turns around the circumference of the hole. According to some embodiments, an aperture radius ($r_{aperture}$) may be about 35% to about 98% $r_{hole}$, and a hole thread radius ($r_{indent}$) is about 36% to about 99% $r_{hole}$. A plate may include a second hole (e.g., a fixed angle hole, a variable angle hole).

According to some embodiments, a variable angle orthopedic plate may comprise a variable angle through hole comprising at least one thread spanning at least one turn (e.g., two turns, three turns, or more) around the circumference of the hole. In some embodiments, each turn may comprise a first region having a maximum thread height ($h_{max1}$), a second region having a maximum thread height ($h_{max2}$), and a third region having a minimum thread height ($h_{min3}$) positioned between the first region and the second region, wherein $h_{max1} > h_{min3}$, $h_{max2} > h_{min3}$, and $h_{min3} > 0$ for each turn independently. The third regions of each turn may be aligned in a column parallel or substantially parallel with the central hole axis. Each turn may comprise, according to some embodiments, a fourth region having a maximum thread height ($h_{max4}$) and a fifth region having a minimum thread height ($h_{min5}$) positioned between the second region and the fourth region, wherein $h_{max2} > h_{min5}$, $h_{max4} > h_{min5}$, and $h_{min5} > 0$, wherein the fifth regions of each turn are aligned in a column parallel or substantially parallel with the central hole axis. In some embodiments, each turn may comprise a sixth region having a maximum thread height ($h_{max6}$) and a seventh region having a minimum thread height ($h_{min7}$) positioned between the fourth region and the sixth region, wherein $h_{max4} > h_{min7}$, $h_{max6} > h_{min7}$, and $h_{min7} > 0$, wherein the seventh regions of each turn are aligned in a column parallel or substantially parallel with the central hole axis. Each turn may comprise a an eighth region having a maximum thread height ($h_{max8}$) and a ninth region having a minimum thread height ($h_{min9}$) positioned between the sixth region and the eighth region, wherein $h_{max6} > h_{min9}$, $h_{max8} > h_{min9}$, and $h_{min9} > 0$, wherein the ninth regions of each turn are aligned in a column parallel or substantially parallel with the central hole axis in some embodiments. Additional regions of maxima and minima may be included in a thread according to some embodiments. Thread regions of minimum height may be, in some embodiments, about equal (e.g., $h_{min3} \approx h_{min5} \approx h_{min7} \approx h_{min9}$) to one another. Thread regions of maximum height may be, in some embodiments, about equal (e.g., $h_{max1} \approx h_{max2} \approx h_{max4} \approx h_{max6} \approx h_{max8}$) to one another. According to some embodiments, a thread may have a minimum thread height ($h_{min3}$) is about 1% to about 80% (e.g., about 5% to about 60%) of maximum thread height ($h_{max1}$).

The circumferential extent of regions of minimum hole thread height and/or maximum hole thread height may be selected as desired some embodiments. The circumferential extent of each region may be represented as $c_{extent}$, wherein $0° < c_{extent1} + c_{extent2} + \ldots c_{extentN} \leq 360°$, where N is the total number of regions of minimum and maximum height. In some embodiments, the circumferential extent of the regions of maximum thread height (e.g., the first region, the second region, the fourth region, the sixth region, and/or the eighth region) may total, for example, more than 120°, more than 150°, more than 180°, more than 210°, and/or more than 240°. The circumferential extent of the regions of maximum thread height (e.g., the third region, the fifth region, the seventh region, and/or the ninth region) may total, for example, less than 120°, less than 150°, less than 180°, less than 210°, and/or less than 240°.

A thread may comprise, according to some embodiments, any desired transition from one region to the next. For example, a transition may be step-wise, graded, or smooth. An orthopedic plate may comprise one variable angle hole and at least one other hole in some embodiments. A second hole may be any type of hole desired including, for example, a fixed angle hole, a variable angle hole (e.g., like the first or different), or a compression hole. A through hole may have any desired symmetric or asymmetric shape including, for example, generally cylindrical, hourglass, inverted hourglass, and others.

A hole thread minimum (e.g., each hole thread minimum) may be selected, in some embodiments, as a function of its adjacent thread maximum. For example, a hole thread minimum may be from about 1% to about 90% of the adjacent hole thread maxima, from about 5% to about 80% of the adjacent thread maxima, from about 10% to about 70% of the adjacent thread maxima, and/or from about 20% to about 60% of the adjacent thread maxima.

A variable angle orthopedic plate may comprise, according to some embodiments, a variable angle through hole comprising at least one thread spanning at least a first turn around the circumference of the hole, the first turn comprising a first region having a maximum thread height ($h_{max1-1}$), a second region having a maximum thread height ($h_{max1-2}$), and a third region having a minimum thread height ($h_{min1-3}$) positioned between the first region and the second region, wherein $h_{max1-1}>h_{min1-3}$, $h_{max1-2}>h_{min1-3}$ and $h_{min1-3}>0$. In some embodiments, the regions of maximum thread height may be approximately equal (e.g., $h_{max1-1} \approx h_{max1-2}$). A minimum thread height ($h_{min1-3}$) may be about 1% to about 80% of maximum thread height ($h_{max1-1}$) in some embodiments. A thread may further comprise, according to some embodiments, a second turn around the circumference of the hole. A second turn may comprise, for example, a first region having a maximum thread height ($h_{max2-1}$), a second region having a maximum thread height ($h_{max2-2}$) and a third region having a minimum thread height ($h_{min2-3}$) positioned between the first region and the second region, wherein $h_{max2-1}$ $h_{min2-3}$, $h_{max2-2}>h_{min2-3}$, and $h_{min2-3}>0$, wherein the third region of the first turn and the third region of the second turn are aligned in a column parallel or substantially parallel with the central hole axis.

The present disclosure relates, in some embodiments, to a variable angle orthopedic fastener (e.g., screw). A variable angle orthopedic fastener (e.g., screw) may comprise, for example, a threaded shank having an upper end and a tip and a head fixed to the upper end of the shank. A head may comprise a core (e.g., a generally cylindrical core) of radius ($r_{core}$) and with a longitudinal axis, a single continuous thread encircling the core, the apex of which defines an outer periphery of radius ($r_{head}$); and/or a thread trough. A thread may have, in some embodiments, at least one indentation along its length, each indentation having a radius ($r_{head-indent}$), wherein $r_{core}<r_{head-indent}<r_{head}$. A variable angle fastener (e.g., screw) may be operable to engage a threaded hole of an orthopedic plate at a first angle aligned with the central hole axis and at least one other angle in some embodiments. In some embodiments, a thread may comprise a plurality of indentations arranged in at least one column (e.g., 2, 3, 4, 5, 6 or more columns), with each column optionally parallel or substantially parallel to the longitudinal axis. Columns may be spaced (e.g., evenly spaced) around the longitudinal axis. A head thread may encircle the full length of a fastener (e.g., screw) head or only a portion of a head (e.g., where a screw head cap is present). The head thread lead, pitch, length, height, width may be selected as desired. For example, a thread may be long enough to encircle the head in one or more turns (e.g., 2, 3, 4 turns or more) in some embodiments. A head and/or thread may be sized so $r_{core}$ is about 25% to about 98% $r_{head}$, and $r_{head-indent}$ is about 26% to about 99% $r_{head}$ or $r_{core}$ is about 25% to about 75% $r_{head}$, and $r_{head-indent}$ is about 26% to about 90% $r_{head}$.

According to some embodiments, a variable angle orthopedic fastener (e.g., screw) may comprise a threaded shank and a head fixed to the shank optionally defining a longitudinal screw axis. A head may comprise, for example, at least one thread spanning at least one turn (e.g., two turns, three turns, or more) around the circumference of the head. Each turn of a thread may comprise a first region having a maximum thread height ($h_{max1}$), a second region having second region having a maximum thread height ($h_{max2}$), and/or a third region having a minimum thread height ($h_{min3}$) positioned between the first region and the second region, wherein $h_{max1}>h_{min3}$, $h_{max2}>h_{min3}$, and $h_{min3}>0$ for each turn independently. In some embodiments, the third regions of each turn are aligned in a column parallel or substantially parallel with the longitudinal axis of the fastener. Each turn may comprise, according to some embodiments, a fourth region having a maximum thread height ($h_{max4}$) and a fifth region having a minimum thread height ($h_{min5}$) positioned between the second region and the fourth region, wherein $h_{max2}>h_{min5}$, $h_{max4}>h_{min5}$, and $h_{min5}>0$, wherein the fifth regions of each turn are aligned in a column parallel or substantially parallel with the longitudinal axis. In some embodiments, each turn may comprise a sixth region having a maximum thread height ($h_{max6}$) and a seventh region having a minimum thread height ($h_{min7}$) positioned between the fourth region and the sixth region, wherein $h_{max4}>h_{min7}$, $h_{max6}>h_{min7}$, and $h_{min7}>0$, wherein the seventh regions of each turn are aligned in a column parallel or substantially parallel with the longitudinal axis. Each turn may comprise a an eighth region having a maximum thread height ($h_{max8}$) and a ninth region having a minimum thread height ($h_{min9}$) positioned between the sixth region and the eighth region, wherein $h_{max6}>h_{min9}$, $h_{max8}>h_{min9}$, and $h_{min9}>0$, wherein the ninth regions of each turn are aligned in a column parallel or substantially parallel with the longitudinal axis in some embodiments. Thread regions of minimum height may be, in some embodiments, about equal (e.g., $h_{min3} \approx h_{min5} \approx h_{min7} \approx h_{min9}$) to one another. Thread regions of maximum height may be, in some embodiments, about equal (e.g., $h_{max1} \approx h_{max2} \approx h_{max4} \approx h_{max6} \approx h_{max8}$) to one another. According to some embodiments, a thread may have a minimum thread height ($h_{min3}$) is about 1% to about 80% (e.g., about 5% to about 60%) of maximum thread height ($h_{max1}$).

The circumferential extent of regions of minimum head thread height and/or maximum head thread height may be selected as desired some embodiments. The circumferential extent of each region may be represented as $c_{extent}$, wherein $0°<c_{extent1}+c_{extent2}+ \ldots c_{extentN} \leq 360°$, where N is the total number of regions of minimum and maximum height. In some embodiments, the circumferential extent of the regions of maximum thread height (e.g., the first region, the second region, the fourth region, the sixth region, and/or the eighth region) may total, for example, more than 120°, more than 150°, more than 180°, more than 210°, and/or more than 240°. The circumferential extent of the regions of maximum thread height (e.g., the third region, the fifth region, the seventh region, and/or the ninth region) may total, for example, less than 120°, less than 150°, less than 180°, less than 210°, and/or less than 240°.

A head thread may comprise, according to some embodiments, any desired transition from one region to the next. For example, a transition may be step-wise, graded, or smooth. A head thread minimum (e.g., each head thread minimum) may be selected, in some embodiments, as a function of its adjacent thread maximum. For example, a head thread minimum may be from about 1% to about 90% of the adjacent head thread maxima, from about 5% to about 80% of the adjacent thread maxima, from about 10% to about 70% of the adjacent thread maxima, and/or from about 20% to about 60% of the adjacent thread maxima. A fastener head may have any desired symmetric or asymmetric shape including, for example, generally cylindrical, hourglass, inverted hourglass, spherical, and others.

A variable angle orthopedic fastener (e.g., screw) may comprise, according to some embodiments, a variable angle through head comprising at least one thread spanning at least a first turn around the circumference of the head, the first turn comprising a first region having a maximum thread height ($h_{max1-1}$), a second region having a maximum thread height ($h_{max1-2}$), and a third region having a minimum thread height ($h_{min1-3}$) positioned between the first region and the second region, wherein $h_{max1-1}>h_{min1-3}$, $h_{max1-2}>h_{min1-3}$, and $h_{min1-3}>0$. In some embodiments, the regions of maximum thread height may be approximately equal (e.g., $h_{max1-1} \approx h_{max1-2}$). A minimum thread height ($h_{min1-3}$) may be about 1% to about 80% of maximum thread height ($h_{max1-1}$) in some embodiments. A thread may further comprise, according to some embodiments, a second turn around the circumference of the head. A second turn may comprise, for example, a first region having a maximum thread height ($h_{max2-1}$), a second region having a maximum thread height ($h_{max2-2}$) and a third region having a minimum thread height ($h_{min2-3}$) positioned between the first region and the second region, wherein $h_{max2-1}>h_{min2-3}$, $h_{max2-2}>h_{min2-3}$, and $h_{min2-3}>0$, wherein the third region of the first turn and the third region of the second turn are aligned in a column parallel or substantially parallel with the longitudinal axis.

The present disclosure relates, in some embodiments, to variable angle orthopedic systems. For example, a system may comprise an orthopedic plate selected from a fixed angle plate and a variable angle plate and an orthopedic fastener (e.g., screw) selected from a fixed angle fastener (e.g., screw) and a variable angle fastener (e.g., screw). A fixed angle plate may comprise an upper surface, a bone facing surface, and one or more holes between the upper surface and the bone facing surface, each hole having a generally cylindrical shape with a central hole axis and comprising a single continuous thread, the apex of which defines a central hole aperture of constant radius ($r_{hole-aperture-constant}$), and a thread trough defining a constant total hole radius of ($r_{hole-constant}$). A variable angle plate optionally may be selected from any variable angle plate disclosed herein. For example, a variable angle plate may comprise an upper surface, a bone facing surface, and at least one variable angle through hole between the upper surface and the bone facing surface, the hole having a generally cylindrical shape with a central hole axis and comprising a single continuous thread, the apex of which defines a central hole aperture of radius ($r_{hole-aperture}$), and a thread trough defining a total hole radius of ($r_{hole}$), wherein the thread has at least one indentation along its length, each indentation having a radius ($r_{hole-indent}$), wherein $r_{aperture}<r_{hole-indent}<r_{hole}$. A fixed angle fastener (e.g., screw) may comprise a threaded shank and a head fixed to the shank, the head comprising a generally cylindrical core of constant radius ($r_{head-core-constant}$) and with a longitudinal axis, a single continuous thread encircling the core, the apex of which defines an outer periphery of constant radius ($r_{head-constant}$), and a thread trough. A variable angle fastener optionally may be selected from any variable angle fastener disclosed herein. For example, a variable angle fastener may comprise a threaded shank and a head fixed to the shank, the head comprising a generally cylindrical core of radius ($r_{head-core}$) and with a longitudinal axis, a single continuous thread encircling the core, the apex of which defines an outer periphery of radius ($r_{head}$), and a thread trough, wherein the thread has at least one indentation along its length, each indentation having a radius ($r_{head-indent}$), wherein $r_{core}<r_{head-indent}<r_{head}$. According to some embodiments, a system includes at least one variable angle device selected from a variable angle plate and a variable angle fastener (e.g., screw). For example, a system may include a variable angle orthopedic plate having a plurality of hole thread indentations arranged in at least one column (e.g., 2, 3, 4, 5, 6 or more columns), each column parallel or substantially parallel to the central hole axis. A variable angle plate may have a variable angle hole aperture radius $r_{hole-aperture}$ of about 35% to about 98% $r_{hole}$, and an indent radius $r_{hole-indent}$ of about 36% to about 99% $r_{hole}$. For example, a system may include a variable angle orthopedic fastener (e.g., screw) having a plurality of head thread indentations arranged in at least one column (e.g., 2, 3, 4, 5, 6 or more columns), each column parallel or substantially parallel to the longitudinal axis of the head thread. A variable angle fastener may have a variable angle screw head core radius $r_{head-core}$ is about 25% to about 98% $r_{head}$, and screw head indentation radius $r_{head-indent}$ is about 26% to about 99% $r_{head}$. In some embodiments, a system may include both a variable angle plate and a variable angle fastener (e.g., screw).

A variable angle orthopedic system may comprise, in some embodiments, at least one fixed angle fastener defining a longitudinal axis and comprising a threaded head, and a threaded shank fixed to the head; and an orthopedic plate comprising at least one through hole defining a central hole axis, and at least one means for receiving the head of the fixed angle fastener in the at least one hole at a 0° angle between the central hole axis and the longitudinal axis and at least one other angle $\alpha$ (e.g., $0<\alpha\leq30°$, $0<\alpha\leq40°$, $0<\alpha\leq50°$. According to some embodiments, a variable angle orthopedic system may comprise a fixed angle plate comprising one or more holes, each hole defining a central hole axis and comprising at least one thread and a variable angle fastener defining a longitudinal axis and comprising a threaded head, a threaded shank fixed to the head, and a means for inserting the head in the at least one hole at a 0° angle between the central hole axis and the longitudinal axis and at least one other angle $\alpha$ (e.g., $0<\alpha\leq30°$, $0<\alpha\leq40°$, $0<\alpha\leq50°$.

The present disclosure relates, in some embodiments, to methods for making a variable angle orthopedic plate. Methods for making a variable angle orthopedic plate may comprise, for example, providing a plate comprising an upper surface and a bone facing surface, forming a through hole (e.g., having a generally cylindrical shape) between the upper surface and the bone facing surface, forming at least one thread encircling the circumference of the hole at least once, the thread apex defining a central hole aperture of radius ($r_{aperture}$), forming at least one trough encircling the circumference of the hole at least once, the thread trough defining a total hole radius of ($r_{hole}$), and/or forming at least one indentation in each of the at least one thread, each indentation having a radius ($r_{indent}$), wherein $r_{aperture}<r_{indent}<r_{hole}$. Forming a hole may comprise, in some embodiments, drilling, boring, perforating, puncturing, piercing, punching or other means for creating or enlarging an opening in a material (e.g., a plate). According to some embodiments, forming at least one thread may comprise tapping, cutting (e.g., die cutting), grinding, milling, lapping, rolling, casting, molding, printing, and other means for creating a thread in a hole. Forming indentations (e.g., 1, 2, 3, 4, 5, 6 or more indentations) in each of the at least one threads may include cutting (e.g., die cutting), milling, grinding, knurling, pressing, bending, and other means for reshaping and/or removing at least a portion of a thread, in some embodiments. Hole thread indentations may be spaced apart (e.g., evenly spaced apart) from one or more other indentations and/or arranged in columns (e.g., where two or more turns of threading are present).

The present disclosure relates, in some embodiments, methods for making a variable angle orthopedic fastener. Methods may include, for example, (a) providing a fastener blank (e.g., having a generally cylindrical shape) that defines a longitudinal axis and comprises a proximal end and a distal end, (b) forming at least one head thread and trough encircling the circumference of the proximal end of the fastener blank at least once, the apex of each head thread defining an outer periphery of radius ($r_{head}$) and the trough of each thread defining a head core of radius ($r_{core}$), and/or (c) forming at least one indentation in each of the at least one threads, each indentation having a radius ($r_{head-indent}$), wherein $r_{core} < r_{head-indent} < r_{head}$. In some embodiments, a method may further comprise forming at least one shank thread encircling the circumference of the distal end of the fastener blank. According to some embodiments, forming a head thread and trough may comprise tapping, cutting (e.g., die cutting), grinding, milling, lapping, rolling, casting, molding, printing, and other means for creating a thread at or near one end of a fastener blank. Shank threads may be formed before, concurrently with, or after head thread formation. Forming indentations (e.g., 1, 2, 3, 4, 5, 6 or more indentations) in each of the at least one threads may include cutting (e.g., die cutting), milling, grinding, knurling, pressing, bending, and other means for reshaping and/or removing at least a portion of a thread, in some embodiments. Head thread indentations may be spaced apart (e.g., evenly spaced apart) from one or more other indentations and/or arranged in columns (e.g., where two or more turns of threading are present).

BRIEF DESCRIPTION OF THE DRAWINGS

Some embodiments of the disclosure may be understood by referring, in part, to the present disclosure and the accompanying drawings, wherein:

FIG. 1A illustrates a perspective view of a plate having a variable angle hole according to a specific example embodiment of the disclosure;

FIG. 1D illustrates a top view of the plate shown in FIG. 1A;

FIG. 1E illustrates a section view of the plate and screw shown in FIG. 1D along section line 1E-1E;

FIG. 1F illustrates a section view of the plate and screw shown in FIG. 1D along section line 1F-1F;

FIG. 2 illustrates a side view of a screw for insertion in a variable angle hole according to a specific example embodiment of the disclosure;

Figure 1B:
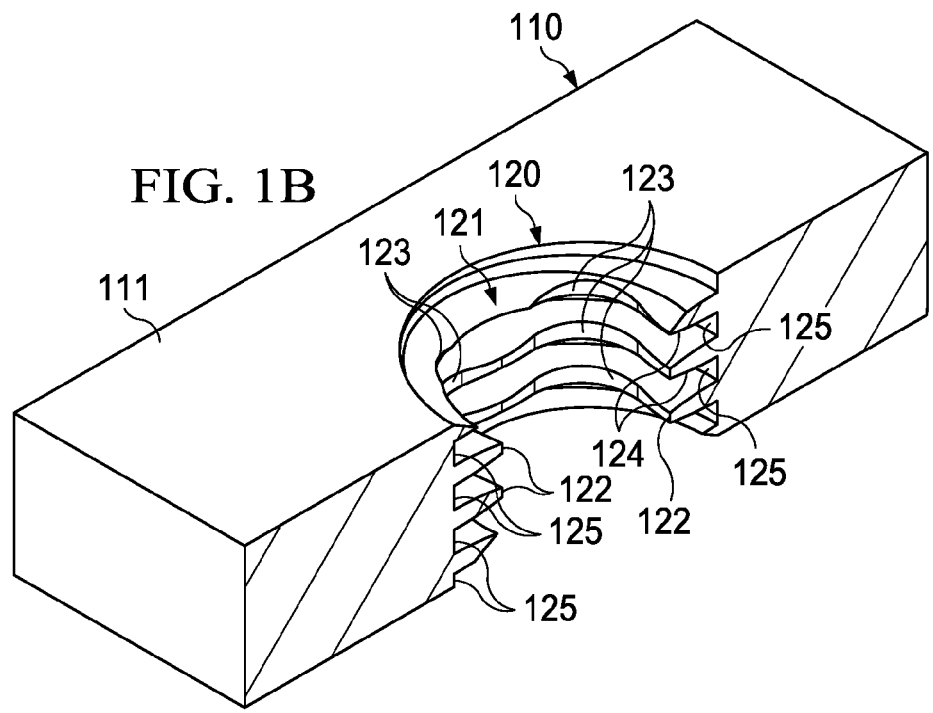
FIG. 1B illustrates a cut-away view of the plate shown in FIG. 1A along a section plane through the thickest portion of the hole threads.

Table 1 below includes the reference numerals used in this disclosure. The hundreds digits correspond to the figure in which the item appears while the tens and ones digits correspond to the particular item indicated. Similar structures share matching tens and ones digits.

| Reference | Detail |
|---|---|
| 0 | System |
| 5 | |
| 10 | Plate |
| 11 | Upper surface |
| 12 | Bone-facing surface |
| 15 | |
| 20 | Hole |
| 21 | Thread |
| 22 | Thread peak |
| 23 | Thread indent |
| 24 | Thread trough |
| 25 | Inner surface |
| 29 | Axis |
| 30 | Screw |
| 31 | Head |
| 32 | Head cap |
| 33 | Head thread |
| 34 | Head thread peak |
| 35 | |
| 36 | Head thread trough |
| 37 | Shank |
| 38 | Shank thread |
| 39 | Axis |
| 40 | Screw |
| 41 | Head |
| 42 | Head cap |
| 43 | Head thread |
| 44 | Head thread peak |
| 45 | Head thread indent |
| 46 | Head thread trough |
| 47 | Shank |
| 48 | Shank thread |
| 49 | Axis |
| 50 | Hole |
| 51 | Thread |
| 52 | Trough |
| 55 | Lateral surface |
| 59 | Axis |

DETAILED DESCRIPTION

The present disclosure relates, in some embodiments, to orthopedic implantable device technology, and more specifically to variable and/or selectable angle implantable devices, systems, and methods. For example, an angle of installing a fixation device into a matrix (e.g., bone) may be varied as desired upon device manufacture, upon device installation, upon system manufacture, upon system assembly, upon system installation, and/or combinations thereof.

Bone Plates

According to some embodiments, the present disclosure relates to implantable plates. An implantable plate may be of any size and shape desired and/or appropriate for being secured to a bone of interest. For example, an implantable plate may comprise a generally flat or contoured body having an upper surface and a bone-facing surface. An upper surface and/or a bone-facing surface may be generally planar in some embodiments. An upper surface and/or bone facing surface may be independently and/or correspondingly contoured. A bone plate may comprise and/or be made from any material suitable for implantation into the body, including, for example, stainless steel, titanium, ceramic, PEEK, a polymeric material, a carbon fiber material, a composite material, and/or combinations thereof, according to some embodiments. A bone plate may permit at least partial load sharing between bones or bone sections that it connects. For example, a bone plate may permit at least partially sharing weight across a bone graft site. It may be desirable, in some embodiments, to permit some movement and/or load to be born by bone (e.g., to facilitate healing). According to some embodiments, a bone plate may be strong enough to resist collapsing forces and/or abnormal angulation during the healing of a bone.

An implantable plate may be secured to a bone using any desired and/or appropriate fastener including, for example, nails, screws, rods, and combinations thereof. It may be desirable, in some embodiments, for a bone plate to be secure in its attachment to the bone (e.g., to resist and/or prevent migration of the implant or back out of the screws from the bone which could result in damage to the structures surrounding the bone, causing potentially severe complications). According to some embodiments, a bone plate may be any object configured to receive one or more (e.g., at least two) bone screws. A bone plate may comprise, in some embodiments, a rigid and/or semi-rigid body with one or more (e.g., at least two) through holes, each configured to receive a bone screw.

A through hole may have a generally cylindrical shape and/or comprise one or more indents and/or one or more protrusions (e.g., threads, thread segments, ridges, bulges, knobs). Each indent may be configured to engage a thread or other protrusion from a bone screw assembly (e.g., from a bone screw assembly head). For example, each indent present may be positioned along the circumference (e.g., in a regular or irregular pattern if there is more than one indent) of a through hole. A hole may include, for example, one or more threads (e.g., a single entry thread, a double entry thread). According to some embodiments, the present disclosure relates to bone plates having at least one through hole having at least one thread. A hole, in some embodiments, may have an aperture radius ($r_{aperture}$) measured from the central hole axis to the hole thread peak. According to some embodiments, a hole may have a total radius ($r_{hole}$) measured from the central axis of the hole to the trough of a hole thread. A hole may have a constant and/or a substantially constant total radius ($r_{hole}$), in some embodiments, through its entire thickness from the upper surface to the lower surface. A hole thread may have a thread height ($h_{thread}$) calculated as the total radius ($r_{hole}$) less the aperture radius ($r_{aperture}$) in some embodiments. A thread height ($h_{thread}$) may be greater than zero along the entire length of the thread according to some embodiments.

An aperture radius ($r_{aperture}$) of a bone plate hole and/or a hole thread height ($h_{thread}$) may be constant along a thread's full length in some embodiments. A radius ($r_{aperture}$) of a variable-angle bone plate hole thread and/or a hole thread height ($h_{thread}$) may vary along the thread's length. For example, a radius ($r_{aperture}$) of a variable-angle bone plate hole thread may vary (e.g., oscillate) between a maximum ($r_{aperture-max}$) and a minimum ($r_{aperture-min}$) value (e.g., stepwise, continuously variable). In some embodiments, aperture maxima may be arranged at the same or substantially the same position about the central axis of a hole, forming an indent in the hole thread. A variable-angle hole may have from about 1 to about 6 indents. According to some embodiments, indents may be arranged in any desired position about the central axis of a hole. For example, indents may be arranged at regular intervals about the central axis of a hole. In specific example embodiments, a hole with n indents may have the indents positioned about every 360°/n around the central axis of the hole. For example, a hole with 3 indents may have the indents positioned every 360°/3=120° about the central axis of the hole (e.g., at about 0°, about 120°, and about 240°).

A maximum radius ($r_{aperture-max}$) (indent) and/or a minimum radius ($r_{aperture-min}$) (thread peak) of a hole thread may be selected as desired and/or required by the conditions of anticipated use according to some embodiments. Similarly, a maximum thread height ($h_{thread-max}$) and/or a minimum thread height ($h_{thread-min}$) may be selected, in some embodiments, as desired and/or required by the conditions of anticipated use.

A minimum thread height ($h_{thread-min}$) may be selected, in some embodiments, in relation to a maximum thread height ($h_{thread-max}$). For example, a minimum thread height ($h_{thread-min}$) may be from about 0% up to (but not including) 100% of a maximum thread height ($h_{t-max}$) (e.g., about 0%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, and/or about 99%).

A maximum aperture radius ($r_{aperture-max}$) of a hole and/or the distance ($d_{indent}$) along a thread between two minima may be selected with respect to the height of a screw head thread (e.g., to afford space for a head thread to pass between two thread maxima). A minimum radius ($r_{aperture-min}$) and/or the distance ($d_{peak}$) along a thread between two maxima may be selected with respect to the purchase desired and/or required with a screw head thread. A hole thread may vary along its length such that only one minimum (e.g., local or global) is positioned between any two global maxima and/or only one maximum (e.g., local or global) is positioned between any two global minima in some embodiments.

Thread regions of interest may be defined by points (e.g., adjacent points) of maximum thread height, average thread height, minimum thread height, inflection, or combinations thereof, according to some embodiments. For example, regions of maximum and/or minimum thread height may be defined by adjacent points of average thread height and/or points of inflection. Regions of interest may be distinct and/or overlap one another. For example, regions of maximum thread height may be defined by adjacent points of minimum thread height and regions of minimum thread height may be defined by adjacent points of maximum thread height, such that the respective regions overlap. Regions of maximum thread height may be defined by adjacent intervening points of average height and, accordingly be distinct from similarly defined regions of minimum thread height.

The circumferential extent of regions of minimum hole thread height and/or maximum hole thread height may be selected, according to some embodiments, as desired. Considerations may include the nature (e.g., fixed or variable angle), height, thickness, pitch, lead, and/or thread count of a hole thread to be engaged. The circumferential extent of each region may be, in some embodiments, independent of one or more other regions and/or co-dependent on one or more other regions. For example, the circumferential extent of regions of minimum thread height may all be the same or substantially the same. The circumferential extent of regions of maximum thread height may all be the same or substantially the same. The circumferential extent of each region may be represented as $c_{extent}$, wherein $0° < c_{extent1} + c_{extent2} + \ldots c_{extentN} \leq 360°$, where N is the total number of regions of minimum and maximum height. In some embodiments, the circumferential extent of each region may be $0° < c_{extent} \leq 360°/N$. Where $n_{min}$ represents the number of regions of minimum height in each turn, the circumferential extent of each region of minimum height (or optionally all regions of minimum height) may be $0° < c_{extent-min} \leq 30°$, $0° < c_{extent-min} \leq 60°$, $0° < c_{extent-min} \leq 90°$, $0° < c_{extent-min} \leq 120°$, $0° < c_{extent-min} \leq 150°$, $0° < c_{extent-min} \leq 180°$, $0° < c_{extent-min} \leq 210°$, $0° < c_{extent-min} \leq 240°$, $0° < c_{extent-min} \leq 270°$, $0° < c_{extent-min} \leq 300°$, $0° < c_{extent-min} \leq 330°$, $0° < c_{extent-min} \leq 360°$, and/or $0° < c_{extent-min} \leq 360°/n_{min}$. Where $n_{max}$ represents the number of regions of maximum height in each turn, the circumferential extent of each region of maximum height (or optionally all regions of maximum height) may be $0° < c_{extent-max} \leq 30°$, $0° < c_{extent-max} \leq 60°$, $0° < c_{extent-max} \leq 90°$, $0° < c_{extent-max} \leq 120°$, $0° < c_{extent-max} \leq 150°$, $0° < c_{extent-max} \leq 180°$, $0° < c_{extent-max} \leq 210°$, $0° < c_{extent-max} \leq 240°$, $0° < c_{extent-max} \leq 270°$, $0° < c_{extent-max} \leq 300°$, $0° < c_{extent-max} \leq 330°$, $0° < c_{extent-max} \leq 360°$, and/or $0° < c_{extent-max} \leq 360°/n_{max}$.

In some embodiments, a maximum ($r_{aperture-max}$) may be less than or equal to the total radius of a hole ($r_{hole}$). An indent, accordingly, may be smooth and contiguous with the thread troughs ($r_{aperture-max} = r_{hole}$) or may be contoured (e.g., notched) with residual head threading ($r_{aperture-max} < r_{hole}$).

A variable angle hole may include, in some embodiments, any number of turns of a hole thread. For example, a variable angle hole may include about 2, about 3, about 4, about 5, or about 6 turns of a hole thread. Each turn may comprise the same number or a different number of indents and/or peaks according to some embodiments. For example, the first turn(s) and/or the last turn(s) may have fewer or no indents than the other turn(s). For example, the first turn(s) and/or the last turn(s) may have fewer peaks (e.g., just one peak) compared to other turn(s). According to some embodiments, each turn of a hole thread may comprise indents and/or peaks of the same or different dimensions compared to other turns of the thread. For example, the first turn(s) and/or the last turn(s) may have shallower indents than the other turn(s). Each turn (e.g., a first turn and/or a last turn) may have 0 to 8 indents. For example, the first turn(s) and/or the last turn(s) may have higher peaks compared to other turn(s).

According to some embodiments, a hole thread having fewer, shallower, or no indents in the upper-most turn and/or lower-most turn may provide additional purchase for an inserted screw. Where the upper-most turn and/or lower-most turn of a hole thread has fewer, shallower, or no indents, the additional purchase may contribute to stronger and/or more durable fixation of the bone. A hole thread having fewer, shallower, or no indents in its upper-most turn and/or lower-most turn may govern (e.g., limit) the degree of angulation of an inserted screw.

Bone Screws

According to some embodiments, the present disclosure relates to bone screws. A bone screw may have, according to some embodiments, a central longitudinal axis and comprise a bone screw shank and a bone screw head. A bone screw shank may be configured to be secured to a matrix (e.g., bone). For example, a bone screw shank may comprise one or more threads along at least a portion of its length.

A head may or may not have the same geometry and/or radius as a shank portion. For example, it may have a shape other than generally cylindric and/or may have a larger or smaller radius as compared to, for example, the average radius of a shank portion, the minimum radius (e.g., sampled at or near the midpoint of a bone screw shank longitudinal axis), the maximum radius, or any other radial metric of the shank portion. A head may comprise, in some embodiments, one or more surfaces configured to receive a corresponding tool to fit (e.g., drive) a screw into position (e.g., screwed into and secured to a matrix). These one or more surfaces may be positioned anywhere on a head including, for example, near the center of a head and/or on a head's circumference. A bone screw head may have a threaded portion and an unthreaded portion. For example, a bone screw head may have a generally cylindrical shape with a top end and a shank end joined to the shank wherein a thread encircles a portion nearer the shank and an unthreaded head cap is positioned nearer the top end.

A bone screw may comprise, for example, a head having a head thread and a shank having a shank thread. A head thread, in some embodiments, may have a radius ($r_{head}$) measured from the longitudinal screw axis to the head thread peak. A head cap may have a radius equal to or greater than the maximum thread head radius ($r_{head}$). A head thread may have a thread height ($h_{headthread}$) calculated as the difference between the distance from the longitudinal screw axis to the head thread peak and the distance from the longitudinal screw axis to the head thread trough.

A radius ($r_{head}$) of a bone screw head thread may be constant along its full length in some embodiments. A radius of a variable-angle bone screw head thread ($r_{head}$) may vary along its length. For example, a radius of a variable-angle bone screw head thread ($r_{head}$) may vary (e.g., oscillate) between a maximum ($r_{head-max}$) and a minimum ($r_{head-min}$) value (e.g., stepwise, continuously variable). In some embodiments, thread minima may be arranged at the same or substantially the same position about the longitudinal axis of a screw, forming an indent. A variable-angle screw may have from about 1 to about 6 indents. According to some embodiments, indents may be arranged in any desired position about the longitudinal axis of a screw. For example, indents may be arranged at regular intervals about the longitudinal axis of a screw. In specific example embodiments, a screw with n indents may have the indents positioned about every 360°/n around the longitudinal axis of a screw. For example, a screw with 3 indents may have the indents positioned every 360°/3=120° about the longitudinal axis of a screw (e.g., at about 0°, about 120°, and about 240°).

A maximum radius ($r_{head-max}$) and/or minimum radius ($r_{head-min}$) of a head thread may be selected as desired and/or required by the conditions of anticipated use according to some embodiments. A minimum radius ($r_{head-min}$) may be selected, in some embodiments, in relation to a maximum head thread radius ($r_{head-max}$). For example, a minimum radius ($r_{head-min}$) may be from about 60% up to (but not including) 100% of a maximum radius ($r_{head-max}$) (e.g., about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, and/or about 99%). A minimum radius ($r_{head-min}$) of a head thread and/or the distance ($d_{indent}$) along a thread between two maxima may be selected with respect to the height of a hole thread (e.g., to afford space for a hole thread to pass between two thread maxima). A maximum radius ($r_{head-max}$) and/or the distance ($d_{peak}$) along a thread between two minima may be selected with respect to the purchase desired and/or required with a hole thread. A head thread may vary along its length such that only one minimum (e.g., local or global) is positioned between any two global maxima and/or only one maximum (e.g., local or global) is positioned between any two global minima in some embodiments.

Thread regions of interest may be defined by points (e.g., adjacent points) of maximum thread height, average thread height, minimum thread height, inflection, or combinations thereof, according to some embodiments. For example, regions of maximum and/or minimum thread height may be defined by adjacent points of average thread height and/or points of inflection. Regions of interest may be distinct and/or overlap one another. For example, regions of maximum thread height may be defined by adjacent points of minimum thread height and regions of minimum thread height may be defined by adjacent points of maximum thread height, such that the respective regions overlap. Regions of maximum thread height may be defined by adjacent intervening points of average height and, accordingly be distinct from similarly defined regions of minimum thread height.

According to some embodiments, the circumferential extent of regions of minimum head thread height and/or maximum head thread height may be selected as desired. Considerations may include the nature (e.g., fixed or variable angle), height, thickness, pitch, lead, and/or thread count of a hole thread to be engaged. The circumferential extent of each region may be, in some embodiments, independent of one or more other regions and/or co-dependent on one or more other regions. For example, the circumferential extent of regions of minimum thread height may all be the same or substantially the same. The circumferential extent of regions of maximum thread height may all be the same or substantially the same. The circumferential extent of each region may be represented as $c_{extent}$, wherein $0° < c_{extent1} + c_{extent2} + \ldots c_{extentN} \leq 360°$, where N is the total number of regions of minimum and maximum height. In some embodiments, the circumferential extent of each region may be $0° < c_{extent} \leq 360°/N$. Where $n_{min}$ represents the number of regions of minimum height in each turn, the circumferential extent of each region of minimum height (or optionally all regions of minimum height) may be $0° < c_{extent-min} \leq 30°$, $0° < c_{extent-min} \leq 60°$, $0° < c_{extent-min} \leq 90°$, $0° < c_{extent-min} \leq 120°$, $0° < c_{extent-min} \leq 150°$, $0° < c_{extent-min} \leq 180°$, $0° < c_{extent-min} \leq 210°$, $0° < c_{extent-min} \leq 240°$, $0° < c_{extent-min} \leq 270°$, $0° < c_{extent-min} \leq 300°$, $0° < c_{extent-min} \leq 330°$, $0° < c_{extent-min} \leq 360°$, and/or $0° < c_{extent-min} \leq 360°/n_{min}$. Where $n_{max}$ represents the number of regions of maximum height in each turn, the circumferential extent of each region of maximum height (or optionally all regions of maximum height) may be $0° < c_{extent-max} \leq 30°$, $0° < c_{extent-max} \leq 60°$, $0° < c_{extent-max} \leq 90°$, $0° < c_{extent-max} \leq 120°$, $0° < c_{extent-max} \leq 150°$, $0° < c_{extent-max} \leq 180°$, $0° < c_{extent-max} \leq 210°$, $0° < c_{extent-max} \leq 240°$, $0° < c_{extent-max} \leq 270°$, $0° < c_{extent-max} \leq 300°$, $0° < c_{extent-max} \leq 330°$, $0° < c_{extent-max} \leq 360°$, and/or $0° < c_{extent-max} \leq 360°/n_{max}$.

In some embodiments, a minimum ($r_{head-min}$) may be greater than or equal to the radius of a core ($r_{core}$) of a screw head (e.g., measured from the longitudinal axis of the screw to the trough of a head thread). A head indent, accordingly, may be smooth and contiguous with a head core ($r_{head-min}=r_{core}$) or may be contoured (e.g., notched) with residual head threading ($r_{head-min}>r_{core}$).

A variable angle fastener may include, in some embodiments, any number of turns of a head thread. For example, a variable angle fastener may include about 2, about 3, about 4, about 5, or about 6 turns of a head thread. Each turn may comprise the same number or a different number of indents and/or peaks according to some embodiments. For example, the first turn(s) and/or the last turn(s) may have fewer or no indents than the other turn(s). For example, the first turn(s) and/or the last turn(s) may have fewer peaks (e.g., just one peak) compared to other turn(s). According to some embodiments, each turn of a head thread may comprise indents and/or peaks of the same or different dimensions compared to other turns of the thread. For example, the first turn(s) and/or the last turn(s) may have shallower indents than the other turn(s). Each turn (e.g., a first turn and/or a last turn) may have 0 to 8 indents. For example, the first turn(s) and/or the last turn(s) may have higher peaks compared to other turn(s).

According to some embodiments, a head thread having fewer, shallower, or no indents in the upper-most and/or lower-most turn may provide additional purchase with a hole into which it is inserted. Where the upper-most turn and/or lower-most turn of a head thread has fewer, shallower, or no indents, the additional purchase may contribute to stronger and/or more durable fixation of the bone. A head thread having fewer, shallower, or no indents in its upper-most turn and/or lower-most turn may govern (e.g., limit) the degree of angulation of an inserted screw. A head thread having fewer, shallower, or no indents in its lower-most turn may be inserted at a desired angle with relative ease.

Bone Fixation Systems

According to some embodiments, the present disclosure relates to systems for securing bone(s). For example, a fixation system may comprise a bone screw and a bone plate. Optionally, a fixation system may comprise, in some embodiments, a bone screw, a bone plate, a variable and/or selectable angle screw, a variable and/or selectable angle plate, and/or combinations thereof.

According to some embodiments, a fixation system may be fastened to one or more bones. For example, a fixation system may be fastened to a single bone (e.g., across a fracture or break) or to two or more bones (e.g., vertebrae). A bone plate may comprise one or more apertures (e.g., from 1 to about 20 apertures). Some apertures (e.g., each aperture) may receive a bone fastener (e.g., bone screw), which fastener may be fitted into a bone drill hole, for example, to fasten the bone plate to bone.

Each member of a fixation system independently may comprise one or more materials suitable for implantation in a subject (e.g., a human and/or a non-human animal). Each member of a fixation system independently may comprise one or more materials capable of providing suitable structural and/or mechanical strength and/or integrity. Examples of suitable materials may include, without limitation, titanium, cobalt, chromium, stainless steel, alloys thereof, and/or combinations thereof. Examples of suitable materials may include, without limitation, plastics, fibers (e.g., carbon fiber) and/or bioabsorbable materials. Each member of a fixation system independently may comprise one or more one or more surface coatings (e.g., for drug delivery, to promote healing, to aid installation, to resist infection, to increase and/or reduce friction between components, and the like).

Variability and/or selectability may be assessed with respect to (a) the angle formed by the intersection of the plane of a plate hole and the central longitudinal axis of a screw inserted therethrough, (b) the angle formed by the intersection of the plane of a bone plate and the central longitudinal axis of a screw inserted therethrough, and/or (c) the angle formed by the intersection of the central hole axis and the central longitudinal axis of a screw inserted therethrough. Variability and/or selectability may arise from whether a variable-angle plate is used with or without a variable angle screw, whether a variable-angle screw is used with or without a variable angle screw, the pitch of a head thread, the number, breadth, and depth of head thread indents, the hitch of a hole thread, the number, breadth, and depth of hole thread indents present, and combinations thereof.

In some embodiments, a variable angle plate system comprising a plate and a fastener may accommodate insertion of the fastener in the plate at a first angle $\alpha_1$ formed by the central hole axis and the longitudinal fastener axis and at least one additional angle $\alpha_2$ formed by the central hole axis and the longitudinal fastener axis. A variable angle $\alpha$ (e.g., $\alpha_1$ and/or $\alpha_2$) may range from about 0° to about 60°, from about 0° to about 50°, from about 0° to about 40°, and/or from about 0° to about 30° according to some embodiments. Insertion of a fastener at an angle normal or substantially normal to a plate hole may comprise, in some embodiments, inserting the fastener such that the central hole axis and the longitudinal fastener axis are co-linear. In some embodiments, a variable angle plate system may accommodate insertion of a fastener in a hole at a first angle normal to the plane of the hole and at least one angle oblique to the plane of the hole.

Methods of Use

The present disclosure relates, according to some embodiments, to a method of securing one or more bones (e.g., bone fixation). For example, a method may comprise installing a bone plate system having a variable angle plate and/or a variable angle screw in a subject. A method may comprise, in some embodiments, drilling a hole, tapping the hole, and threading a bone screw into a bone. A method may comprise installing a self-drilling screw without pre-drilling and/or without tapping according to some embodiments. A guide may be held next to or attached to a plate in some embodiments. A drill may be inserted, according to some embodiments, into the guide and the hole drilled into the bone. A guide, if used, may be removed and a tap may be threaded through the hole (e.g., following the same or substantially the same angle as a drill hole. It may be desirable to proceed with caution, for example, to prevent the sharp edges of the tap from damaging surrounding tissues or in creating too large a tap hole by toggling the handle of the tap. This damage may reduce the security of the screw bite into the bone and/or increase the likelihood of screw pullout. After tapping, a screw may be guided at a proper angle into a hole that has been created. In some embodiments, inadvertent misalignment may reduce pullout strength and/or may result in damage to surrounding nerves or arteries.

Installing a fastener (e.g., a screw) may include, in some embodiments, varying the angle of insertion (e.g., the central longitudinal axis of the inserted screw) such that is not aligned or parallel with the central hole axis. Installing a fastener (e.g., a screw) may include, in some embodiments, selecting an angle of insertion (e.g., the central longitudinal axis of the inserted screw) that is not aligned or parallel with the central hole axis. Varying an insertion angle may include varying and selecting an insertion angle. Selecting an insertion angle may include varying and selecting an insertion angle.

In some embodiments, a method may comprise contacting a bone plate system comprising at least one variable angle fastener with a bone of subject, inserting the fastener in the bone at an insertion angle that is not aligned or parallel with the central hole axis, and/or combinations thereof. For example, inserting may be optionally repeated for up to all of the fasteners in the bone plate system.

A method of bone fixation may be used to address (e.g., prevent, treat, ameliorate, ease, and/or relieve) one or more conditions and/or symptoms thereof. Conditions that may be addressed include, according to some embodiments, traumatic conditions, pathological conditions, developmental conditions, degenerative conditions, and/or combinations thereof. For example, a method of bone fixation may be used to address degenerative disc disease, spondylolisthesis, a bone fracture or break, spinal stenosis, deformities (e.g., scoliosis, kyphosis and/or lordosis), tumor, pseudoartrosis, necrosis, a bulging or herniated disc, arthrodesis, and combinations thereof. In some embodiments, a method of bone fixation may be applied to any bone(s) in a subject body. A method may be applied, for example, to a subject's foot, hand, clavicle, spine, humerous, radius, ulna, femur, tibia, fibula, and/or combinations thereof. A healthcare professional exercising reasonable prudence and care may determine which embodiment is most desirable for a particular subject.

Methods of Manufacture

In some embodiments, the present disclosure relates to methods of manufacturing variable angle devices and/or systems. For example, a variable angle plate may be made by providing a plate with an upper surface, a bone-facing surface, and at least one hole, tapping the at least one hole to form at least one thread and at least one trough, and forming at least one column of indents in the thread. A column of indentations may have a depth that leaves at least some residual thread such that the threading is reduced but not altogether eliminated in the indentations. Providing a plate with an upper surface, a bone-facing surface, and at least one hole may include providing a plate with an upper surface and a bone-facing surface and drilling at least one hole through the plate. Forming an indentation in a thread (e.g., a column of indents) may include, according to some embodiments, grinding away a portion of a thread, for example, along one, two, three, four, five, or six zones that are substantially parallel to the central axis of a hole. In some embodiments, a method of making a variable angle plate may include deburring, smoothing, polishing and/or coating (e.g., a thread, an indentation, a hole, a plate) as desired and/or required.

Figure 1C:
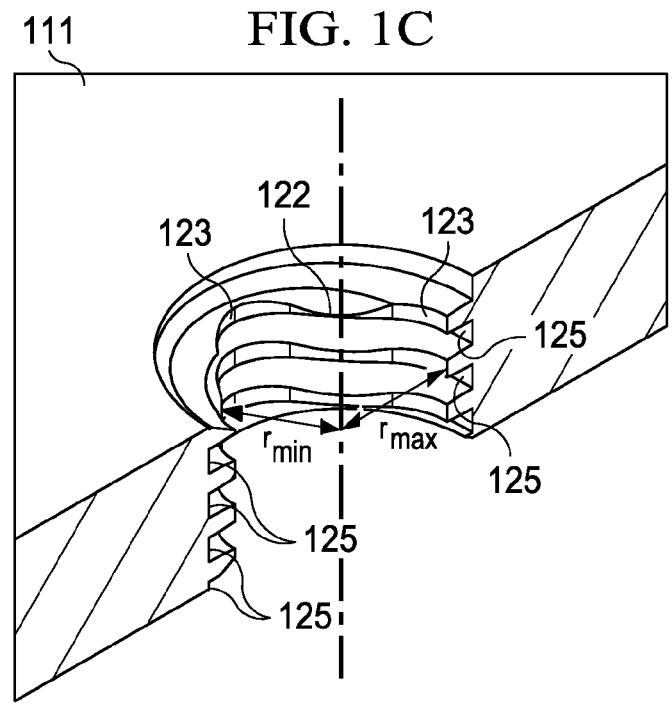
FIG. 1C illustrates a cut-away view of the plate shown in FIG. 1A along a section plane through the shallowest portion of the hole threads.

Making a variable angle screw may comprise providing a blank, forming a head and a shank on the blank to produce a variable angle screw blank, providing a purchase point on the head of the screw blank (e.g., a slot, a cross, or other feature that allows torque to be applied to the screw), cutting (e.g., die cutting) threads into the head of the screw blank, cutting (e.g., die cutting) into the shank of the screw blank, and/or forming at least one column of indents in the head thread. A column of head thread indentations may have a depth that leaves at least some residual thread such that the threading is reduced but not altogether eliminated in the indentations. A method of making a variable angle screw may include, according to some embodiments, deburring, smoothing, polishing and/or coating (e.g., a thread, an indentation, a head, a screw) as desired and/or required Specific Example Embodiments Specific example embodiments of a variable angle plate are illustrated in FIGS. 1A-1F. Variable angle plate 110 comprises an upper surface 111, a bone-facing surface 112, and at least one variable angle hole 120. Upper surface 111 and/or bone-facing surface 112 may be generally planar in some embodiments. Upper surface 111 and/or bone facing surface 112 may be independently and/or correspondingly contoured. Variable angle hole 120 has a generally cylindrical shape with continuous thread 121 and adjoining thread trough 125 around its circumference. Thread 121 comprises four sets of thread peaks 122 and indents 123 spaced apart at regular intervals. FIG. 1B is a cut away view illustrating hole 120 along a section plane that bisects thread 121 at its maximum height ($h_{thread-max}$). FIG. 1C is a cut away view illustrating hole 120 along a section plane that bisects thread 121 at its minimum height ($h_{thread-min}$).

The distance from central hole axis 129 to thread peak 122 corresponds to the minimum aperture radius ($r_{min}$) and the distance from central hole axis 129 to indent 123 corresponds to the maximum aperture radius ($r_{max}$) as shown in FIG. 1C. The distance from central hole axis 129 to lateral surface 125 corresponds to the total hole radius ($r_{hole}$). Plate 110 may further comprise one or more additional holes. Each additional hole may independently be a variable angle hole, a fixed angle hole, a compression hole, an unthreaded hole (e.g., to receive a nail), and combinations thereof.

FIG. 1D is a top view of hole 120 showing that peaks 122 and indents 123 are uniform in each turn of thread 121. FIG. 1E is a section view illustrating hole 120 along a section plane that bisects thread 121 at its maximum height ($h_{thread-max}$). FIG. 1F is a cut away view illustrating hole 120 along a section plane that bisects thread 121 at its minimum height ($h_{thread-min}$).

A specific example embodiment of a bone screw is illustrated in FIG. 2. Bone screw 230 comprises head 231 and shank 237. As shown, head 231 has a generally cylindrical shape and comprises an upper portion with untreaded head cap 232 and a lower portion with head thread 233. Thread 233 comprises thread peak 234 and thread trough 236. Thread peak 234 has a radius ($r_{head}$) that is substantially the same as head cap 232 and does not vary along its length. Shank 237 has a generally cylindrical shape and comprises shank thread 238 encircling its length. The radius of shank thread 238 is substantially smaller than the head thread radius ($r_{head}$). In some embodiments, head thread 233 and shank thread 238 need not be distinct as shown.

Figure 3A:
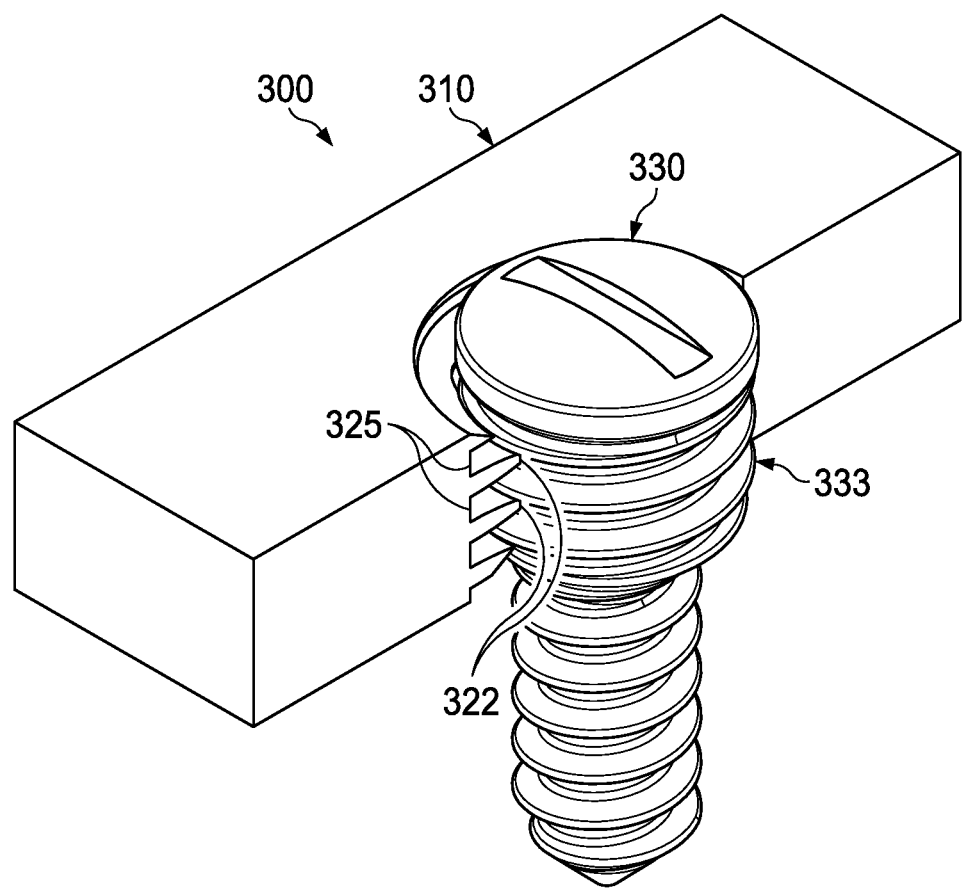
FIG. 3A illustrates a cut-away view of a plate like the one shown in FIG. 1 with a screw like the one shown in FIG. 2 inserted.
Figure 3B:
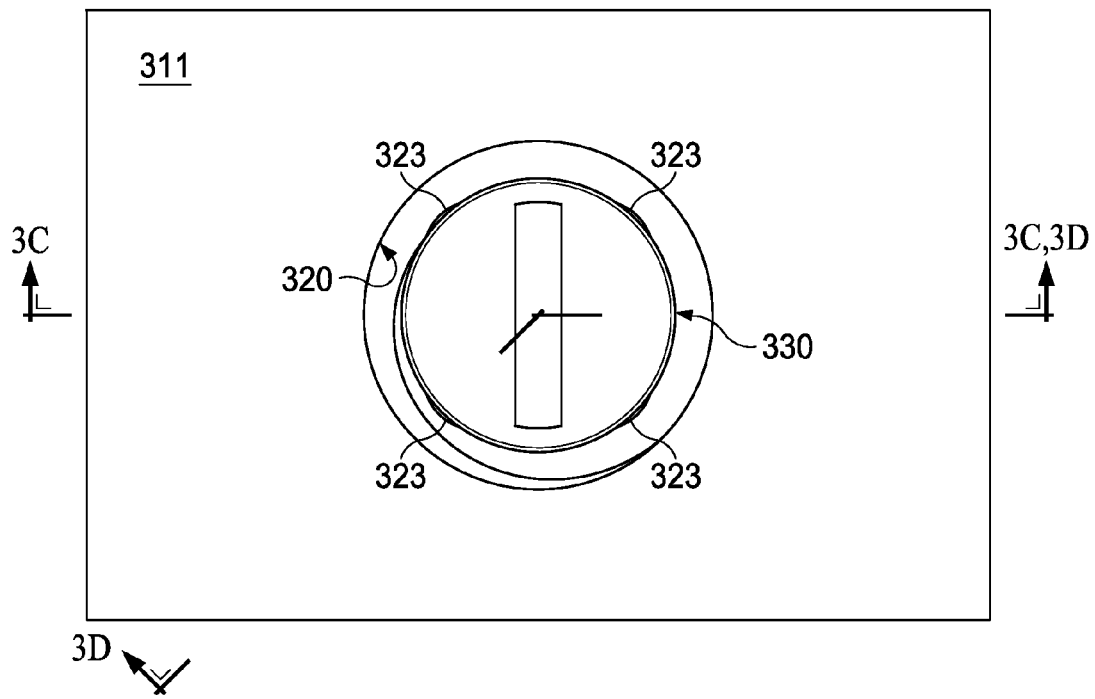
FIG. 3B illustrates a top view of the plate with an inserted screw shown in FIG. 3A.
Figure 3C:
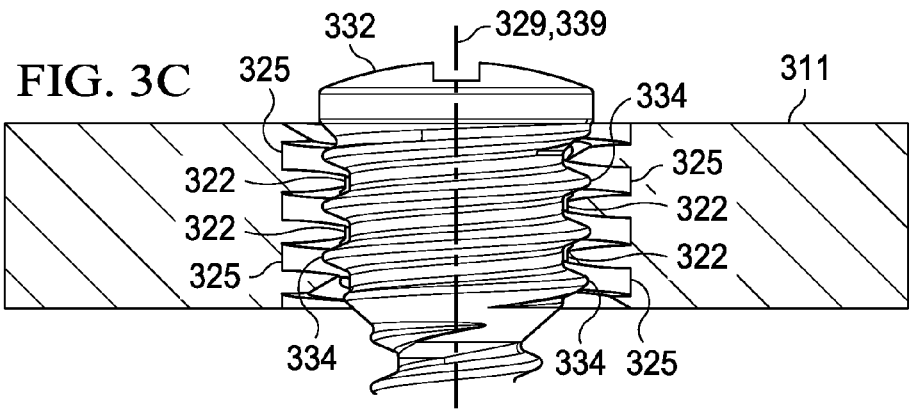
FIG. 3C illustrates a section view of the plate and screw shown in FIG. 3B along section line 3C-3C.
Figure 3D:
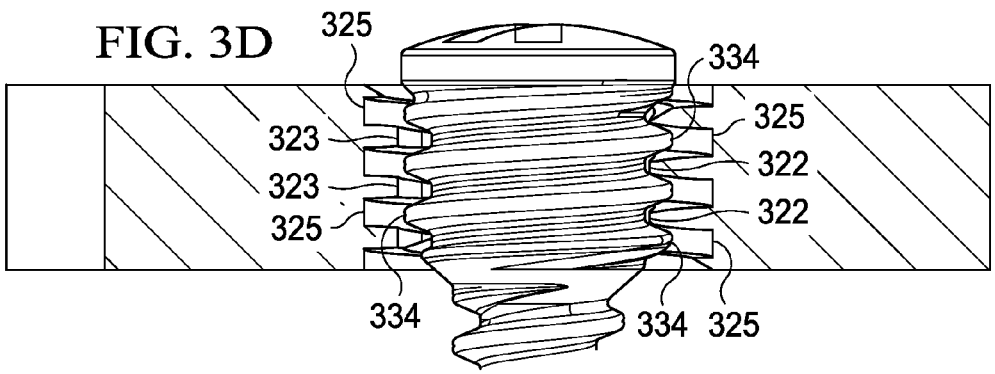
FIG. 3D illustrates a section view of the plate and screw shown in FIG. 3B along section line 3D-3D.
Figure 3E:
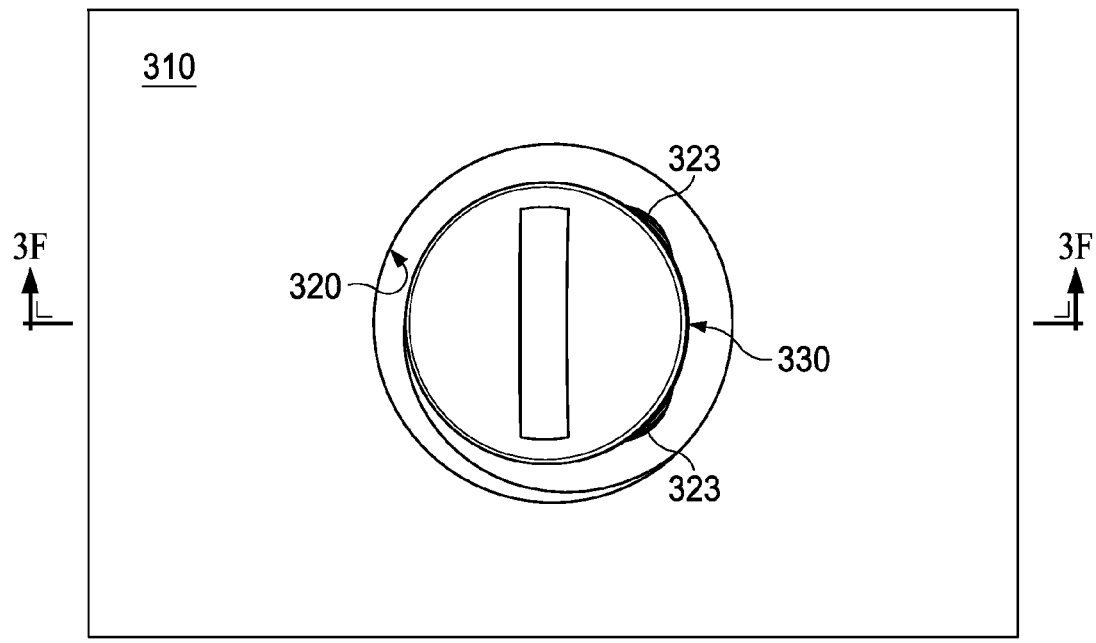
FIG. 3E illustrates a top view of the plate and screw shown in FIG. 3A.
Figure 3F:
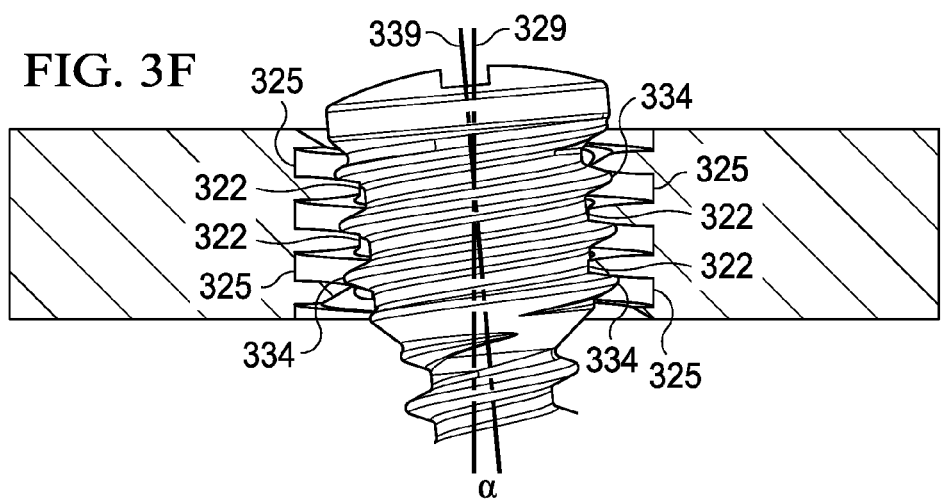
FIG. 3F illustrates a section view of the plate shown in FIG. 3E along section line 3F-3F.

Specific example embodiments of a variable-angle system are illustrated in FIGS. 3A-3F. Variable-angle system 300 comprises variable angle plate 310 and bone screw 330. As shown, screw 330 may be inserted in hole 320 such that longitudinal axis 339 of screw 330 aligns with central hole axis 329 (FIGS. 3A-3D). Screw 330 may be inserted in hole 320 such that longitudinal axis 339 of screw 330 intersects central hole axis 329 and forms (non-zero) angle α (FIGS. 3E-3F). FIG. 3A is a cut away view illustrating hole 320 and screw 330 along a section plane that bisects hole thread 321 at its maximum height ($h_{thread-max}$). Head thread 333 engages hole thread 321 and shank 337 extends below lower surface 312 of plate 310 where it may engage an underlying matrix (e.g., bone). FIG. 3B is a top view of plate 310 with screw 330 inserted in hole 320. FIG. 3C is a section view illustrating hole 320 along a section plane that bisects hole thread 321 at its maximum height ($h_{thread-max}$). FIG. 3D is a cut away view illustrating hole 320 along a section plane that bisects hole thread 321 at its minimum height ($h_{thread-min}$). As shown, head thread 333 engages thread peaks 322, but does not reach indents 323 or lateral surface 325. Head cap 332 may extend above upper surface 311 as illustrated or may be seated in hole 320 such that it is flush with upper surface 332. For example, thread 321 may extend upward from lower surface 312 through hole 320 to a point sufficiently short of upper surface 311 to allow hole 320 to receive head cap 332.

FIG. 3E is a top view of plate 310 with screw 330 inserted in hole 320 at an angle α. FIG. 3F is a section view illustrating hole 320 along a section plane that bisects hole thread 321 at its maximum height ($h_{thread-max}$). FIG. 3F further illustrates intersection of hole axis 329 and head axis 339 to form an angle α. According to some embodiments, axes 329 and 339 may be skew. Projections of skew axes 329 and 339 on a single plane (e.g., a plane parallel to either axis) may intersect to form an angle α.

Figure 4A:
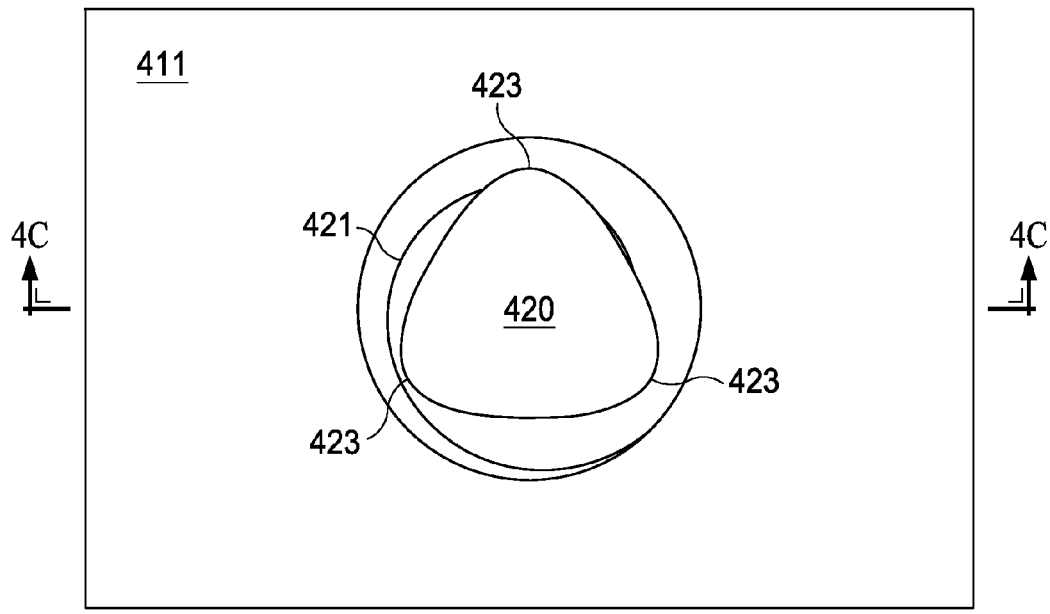
FIG. 4A illustrates a top view of a plate having a variable angle hole according to a specific example embodiment of the disclosure.
Figure 4B:
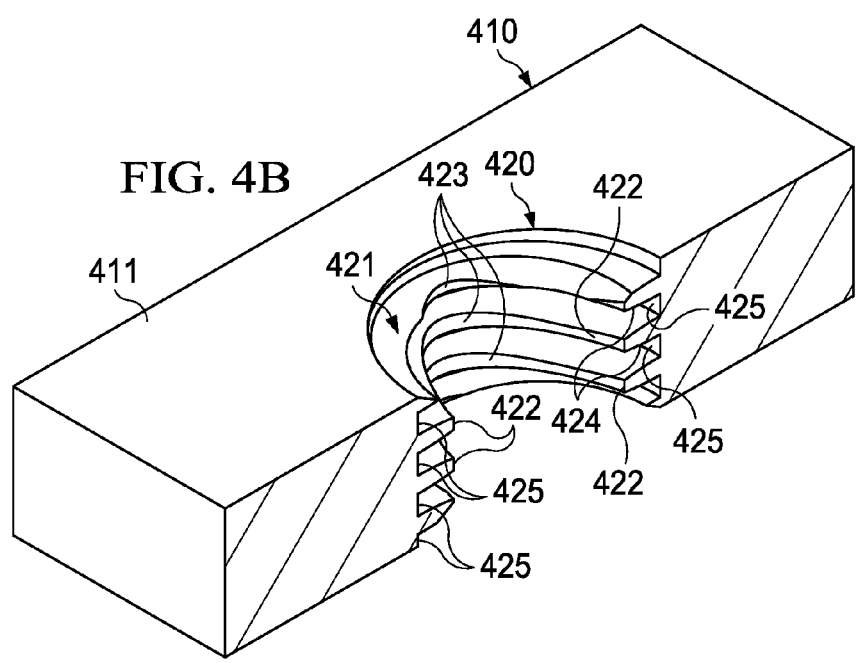
FIG. 4B illustrates a cut-away view of the plate shown in FIG. 4A along a section plane through the thickest portion of the hole threads.
Figure 4C:
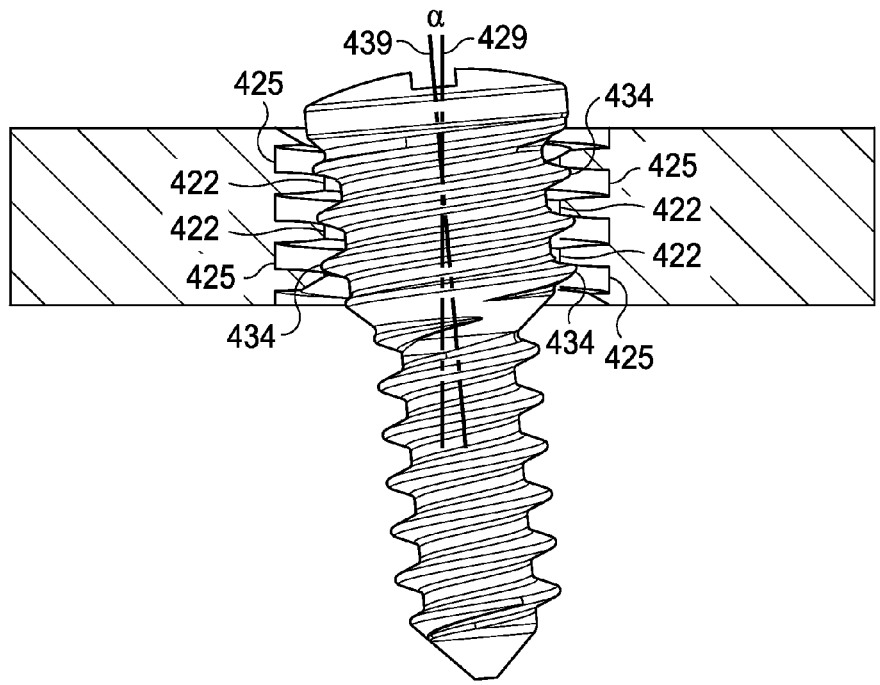
FIG. 4C illustrates a section view of the plate shown in FIG. 4A with the screw shown in FIG. 2 inserted.

Specific example embodiments of a variable angle plate are illustrated in FIGS. 4A-4C. Variable angle plate 410 comprises an upper surface 411, a lower surface 412, and at least one variable angle hole 420. Variable angle hole 420 has a generally cylindrical shape with continuous thread 421 and adjoining thread trough 425 around its circumference. Thread 421 comprises three sets of thread peaks 422 and indents 423 spaced apart at regular intervals. FIG. 4A is a top view of plate 410 with screw 430 inserted in hole 420. FIG. 4B is a section view illustrating hole 420 along a section plane that bisects hole thread 421 at an intermediate height. FIG. 4C is a section view of system 400 comprising plate 410 and screw 430 inserted in variable angle hole 420. As shown, hole axis 429 intersects with head axis 439 to form an angle α.

Figure 5A:
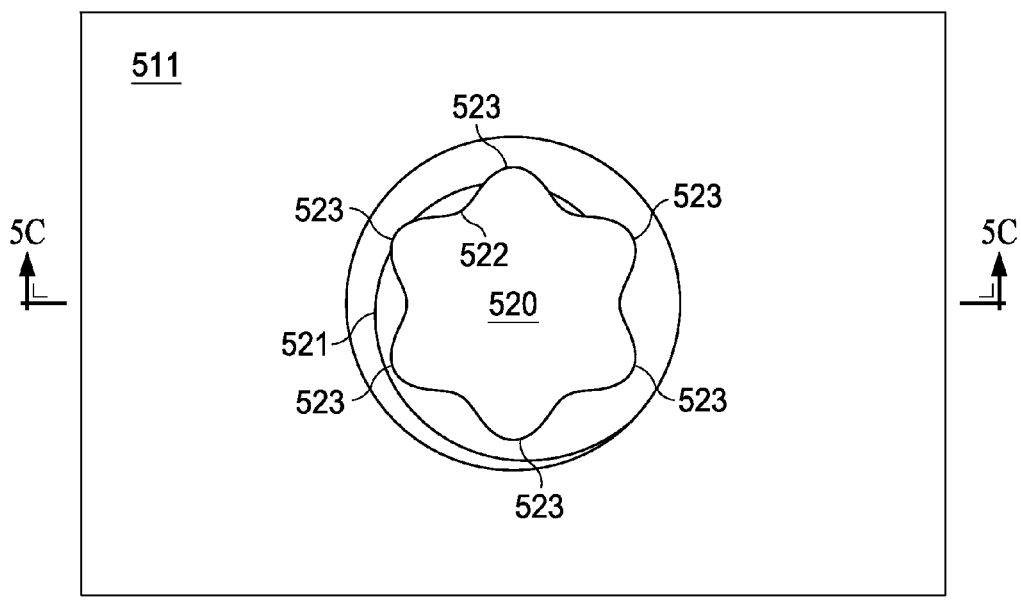
FIG. 5A illustrates a top view of a plate having a variable angle hole according to a specific example embodiment of the disclosure.
Figure 5B:
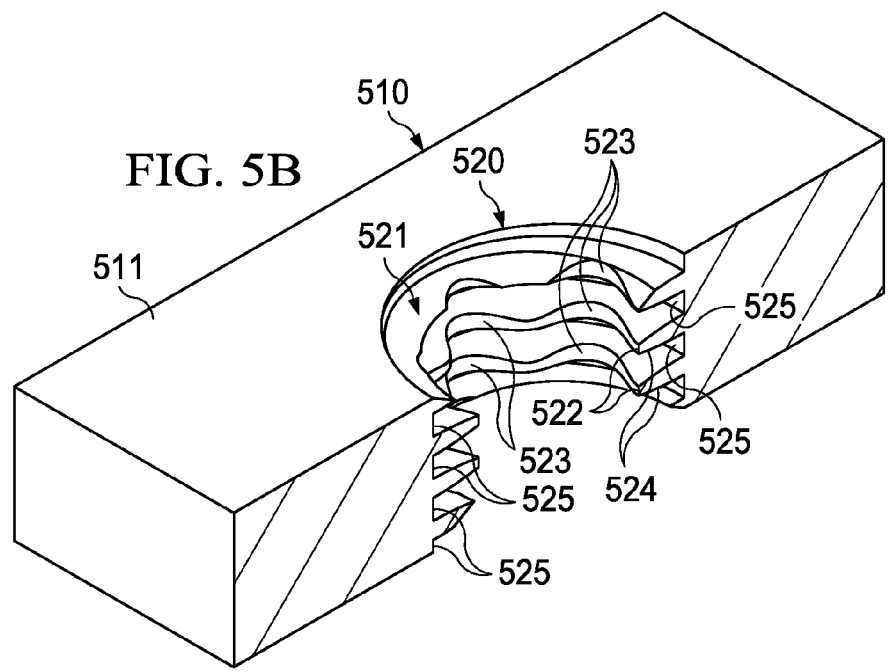
FIG. 5B illustrates a cut-away view of the plate shown in FIG. 5A along a section plane through the thickest portion of the hole threads.
Figure 5C:
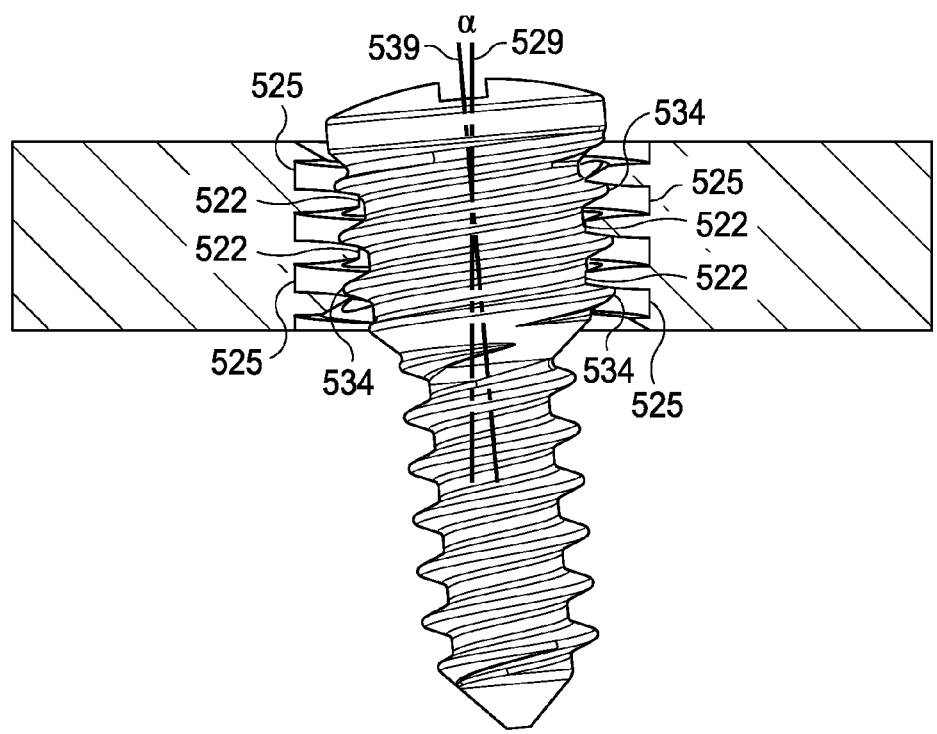
FIG. 5C illustrates a section view of the plate shown in FIG. 5A with a screw like the one shown in FIG. 2 inserted.

Specific example embodiments of a variable angle plate are illustrated in FIGS. 5A-5C. Variable angle plate 510 comprises an upper surface 511, a lower surface 512, and at least one variable angle hole 520. Variable angle hole 520 has a generally cylindrical shape with continuous thread 521 and adjoining thread trough 525 around its circumference. Thread 521 comprises six sets of thread peaks 522 and indents 523 spaced apart at regular intervals. FIG. 5A is a top view of plate 510 with screw 530 inserted in hole 520. FIG. 5B is a perspective view illustrating hole 520 along a section plane that bisects hole thread 521 at its maximum height ($h_{thread-max}$). FIG. 5C is a section view of system 500 comprising plate 510 and screw 530 inserted in variable angle hole 520. As shown, hole axis 529 intersects with head axis 539 to form an angle α.

Figure 6A:
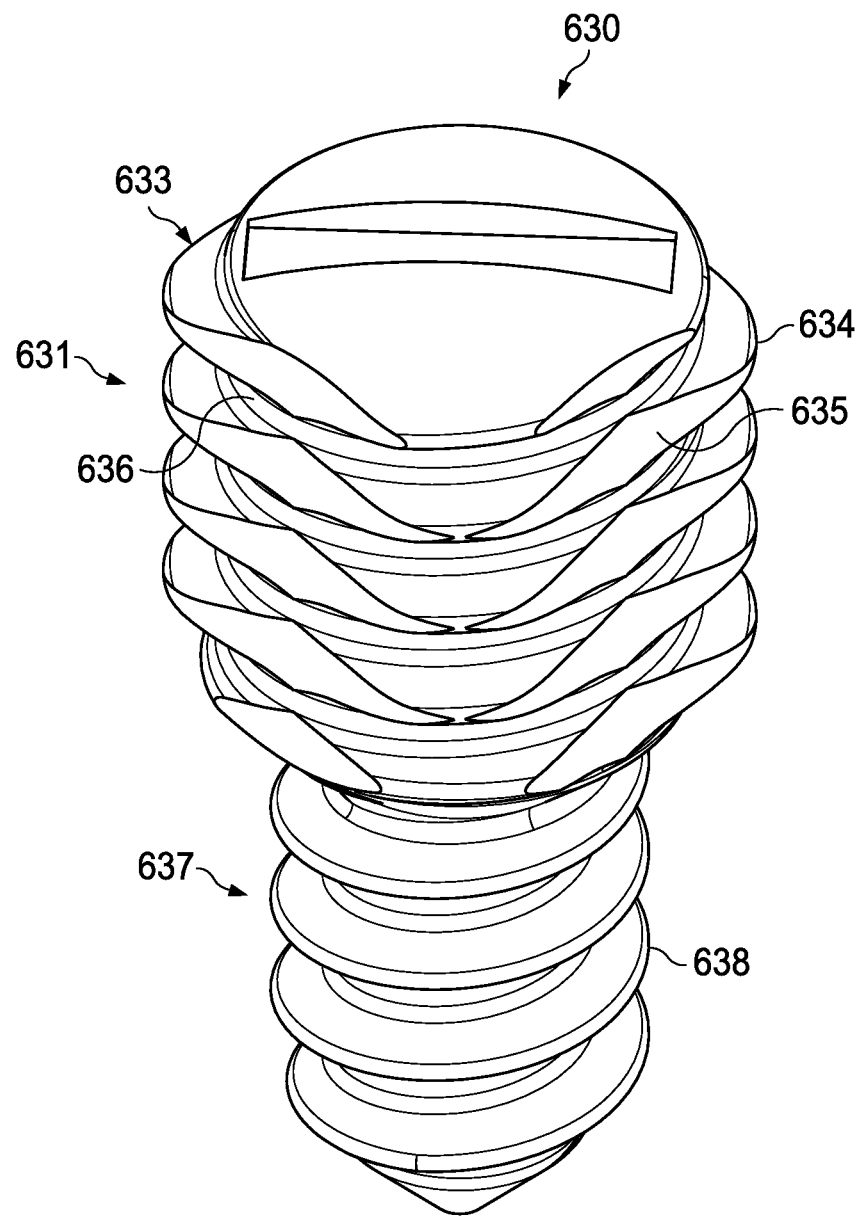
FIG. 6A illustrates a perspective view of a screw for insertion in a variable angle hole according to a specific example embodiment of the disclosure.
Figure 6B:
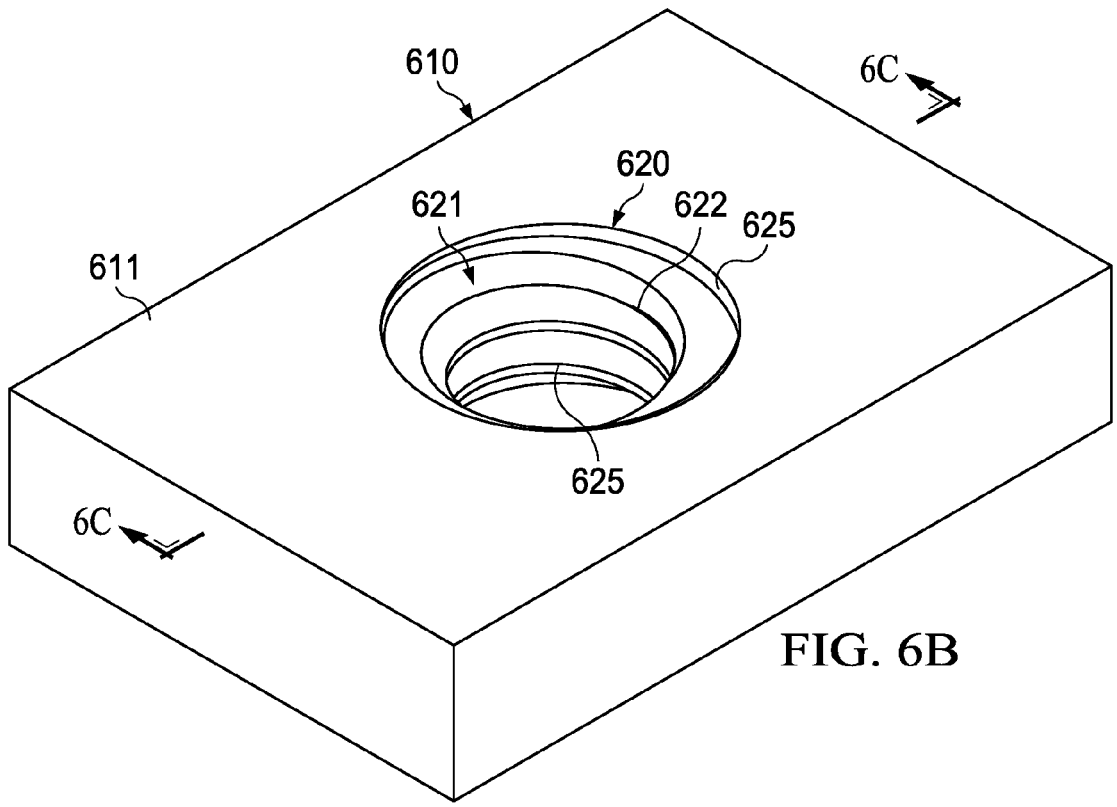
FIG. 6B illustrates a perspective view of a bone plate with a single hole with a uniform thread
Figure 6C:
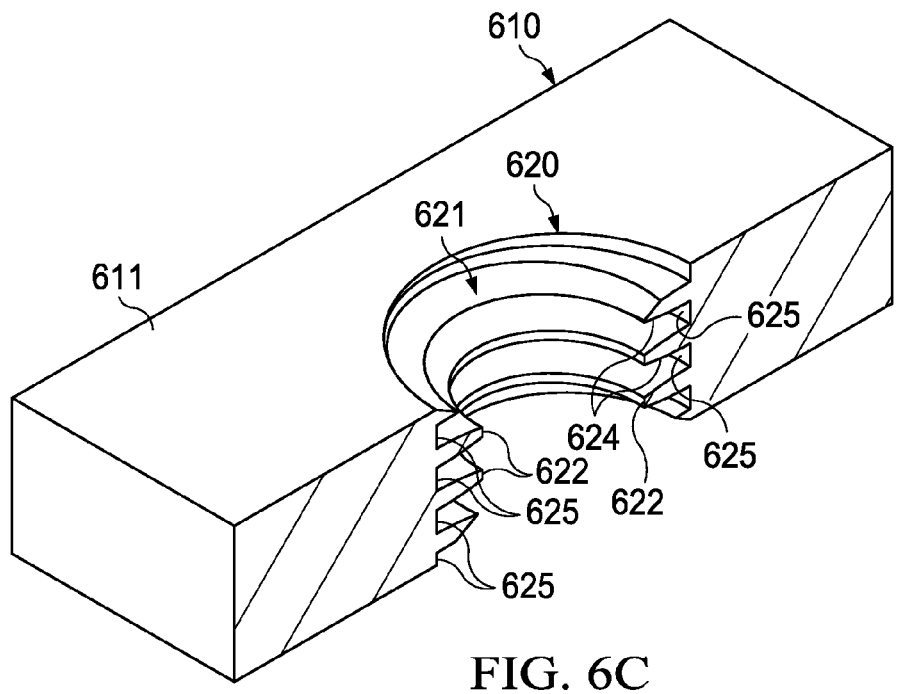
FIG. 6C illustrates a section view of the plate shown in FIG. 6B along section line 6C-6C.
Figure 6D:
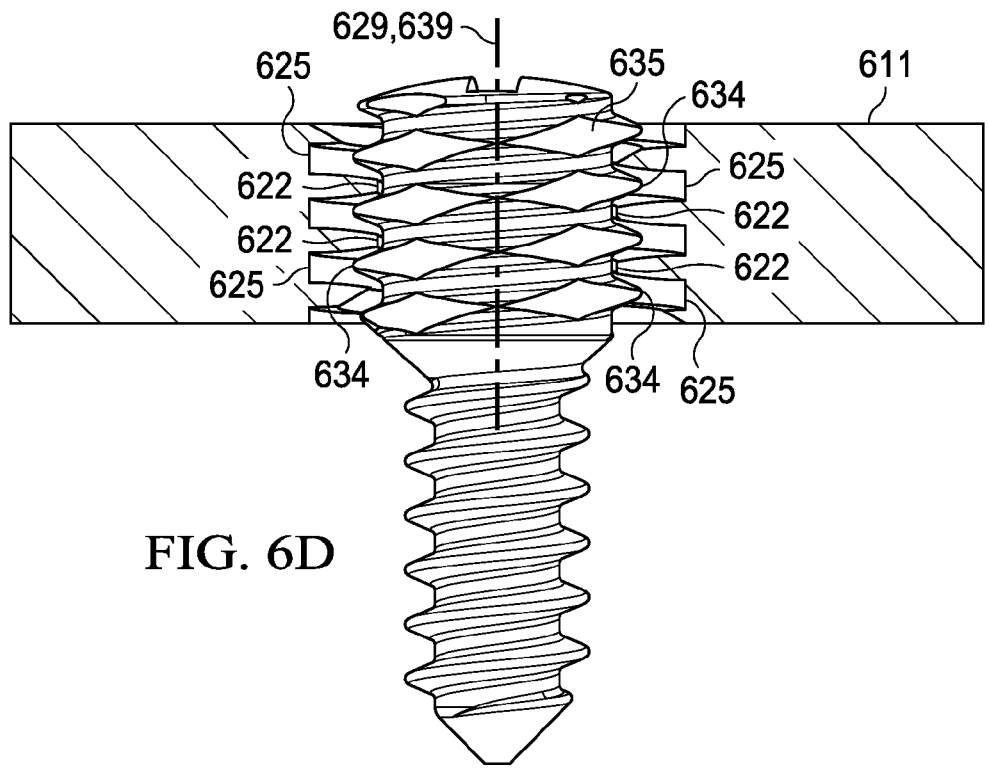
FIG. 6D illustrates a section view (along section line 6C-6C) of the screw shown in FIG. 6A inserted in the plate shown in FIG. 6B with its axis aligned with the hole axis according to a specific example embodiment of the disclosure.

Specific example embodiments of a variable angle bone screw are illustrated in FIGS. 6A-6E. Variable angle screw 640 comprises head 641 and shank 647. As shown, head 641 has a generally cylindrical shape and comprises head thread 643 running from the upper end to the end that joins shank 647. Thread 643 comprises thread peak 644 and thread trough 646. Thread peak 644 has a radius ($r_{head}$) that varies along its length. Shank 647 has a generally cylindrical shape and comprises shank thread 648 encircling its length. The radius of shank thread 648 is substantially smaller than the head thread radius ($r_{head}$). In some embodiments, head thread 643 and shank thread 648 need not be distinct as shown. Head thread 643 comprises four sets of thread peaks 644 and indents 645 spaced apart at regular intervals. FIG. 6A is a perspective view of variable angle screw 640 with its head portion 641 and shank portion 647. FIG. 6B is a perspective view of bone plate 610 having hole 650. As shown, hole 650 comprises thread 651 and trough 652. FIG. 6C is a section view of bone plate 610. Thread 651 and trough 652, as illustrated, encircle hole 650 substantially uniformly. FIG. 6D is a section view of variable angle system 600, which comprises bone plate 610 and screw 640. As shown, screw 640 may be inserted in hole 650 such that longitudinal axis 649 of screw 640 aligns with central hole axis 659. Hole thread 651 engages head thread 643, but does not reach indents 645 or lateral surface 655. Shank 647 extends below lower surface 612 of plate 610 where it may engage an underlying matrix (e.g., bone). The distance from longitudinal screw axis 649 to thread peak 644 corresponds to the maximum radius ($r_{head-max}$) and the distance from longitudinal screw axis 649 to indent 645 corresponds to the minimum radius ($r_{head-min}$) as shown in FIG. 6D. The minimum thread radius ($r_{head-min}$) is the same as the radius of the core of head 641. Thus, thread 643 is discontinuous in that it has zero thread height at indents 645.

Figure 6E:
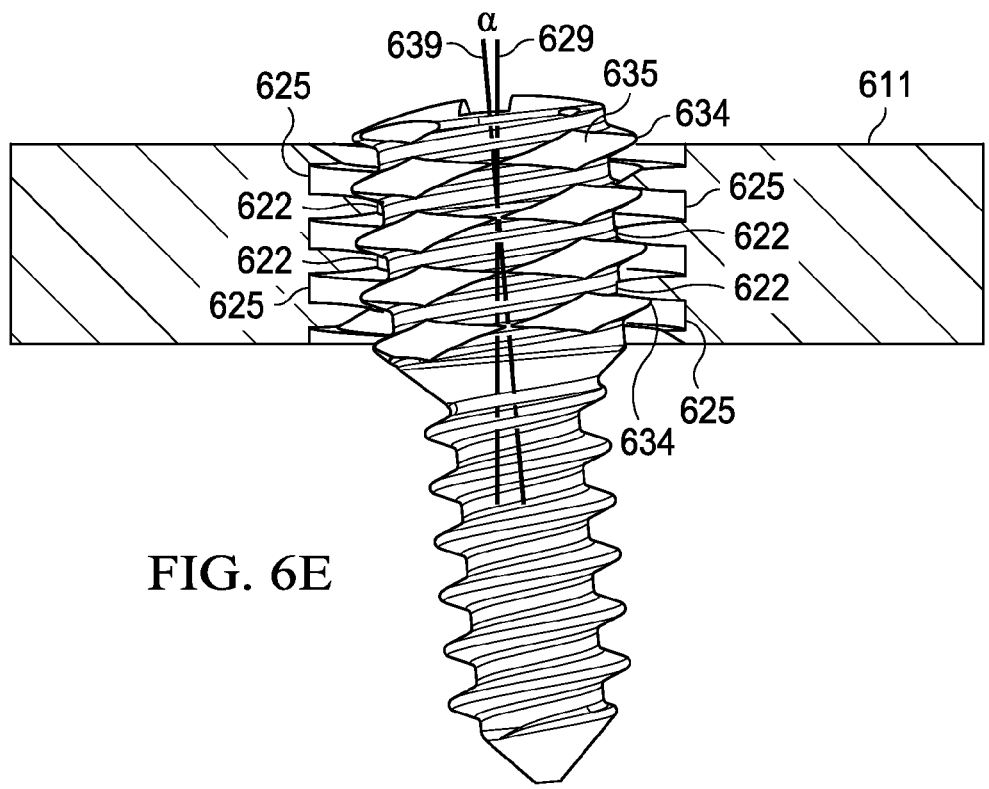
FIG. 6E illustrates a section view (along section line 6C-6C) of the screw shown in FIG. 6A inserted in the plate shown in FIG. 6B with its axis intersecting the hole axis according to a specific example embodiment of the disclosure.

FIG. 6E is a section view illustrating system 600 with variable angle screw 640 inserted in hole 650 such that head axis 649 intersects central hole axis 659 to form an angle α. According to some embodiments, axes 649 and 659 may be skew. Projections of skew axes 649 and 659 on a single plane (e.g., a plane parallel to either axis) may intersect to form an angle α. Plate 610 may further comprise one or more additional holes. Each additional hole may independently be a variable angle hole, a fixed angle hole, a compression hole, an unthreaded hole (e.g., to receive a nail), and combinations thereof.

Figure 7:
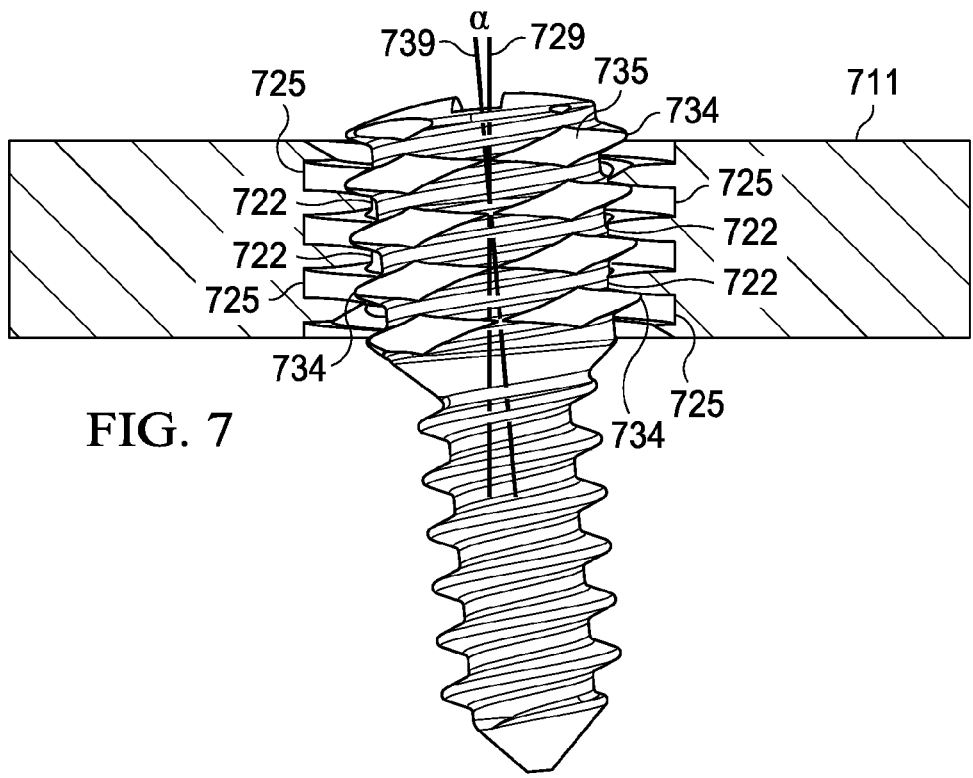
FIG. 7 illustrates a section view of a screw like the one shown in FIG. 6A inserted in a plate like the one shown in FIG. 1B with the head axis intersecting the hole axis according to a specific example embodiment of the disclosure.

Specific example embodiments of a variable angle system are illustrated in FIG. 7. Variable angle system 700 comprises variable angle plate 710 and variable angle screw 740. As shown, variable angle screw 740 is inserted in variable angle hole 720 with head axis 749 intersecting hole axis 729 to form angle β. Indents 723 and indents 745 are aligned such that head thread peaks 744 engage hole thread peaks 722 but do not reach lateral surface 725.

Figure 8A:
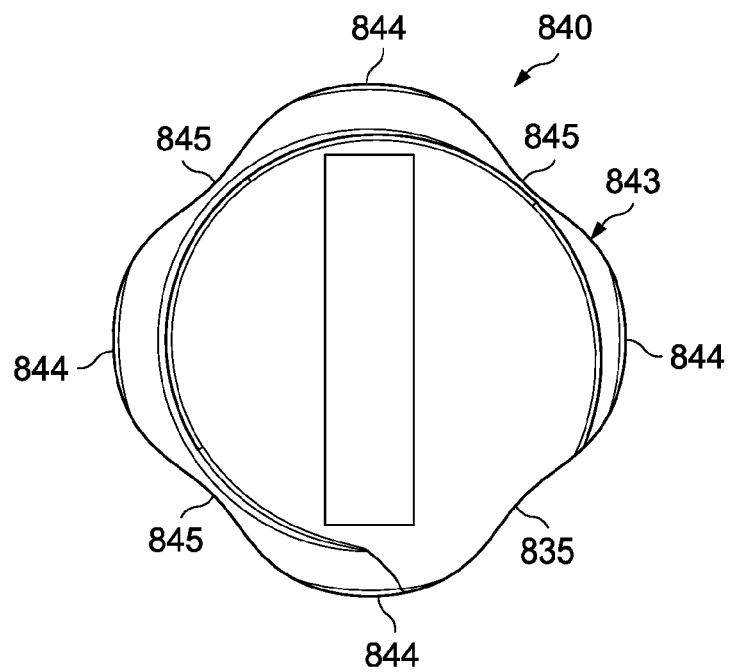
FIG. 8A illustrates a top view of a screw for insertion in a variable angle hole according to a specific example embodiment of the disclosure.
Figure 8B:
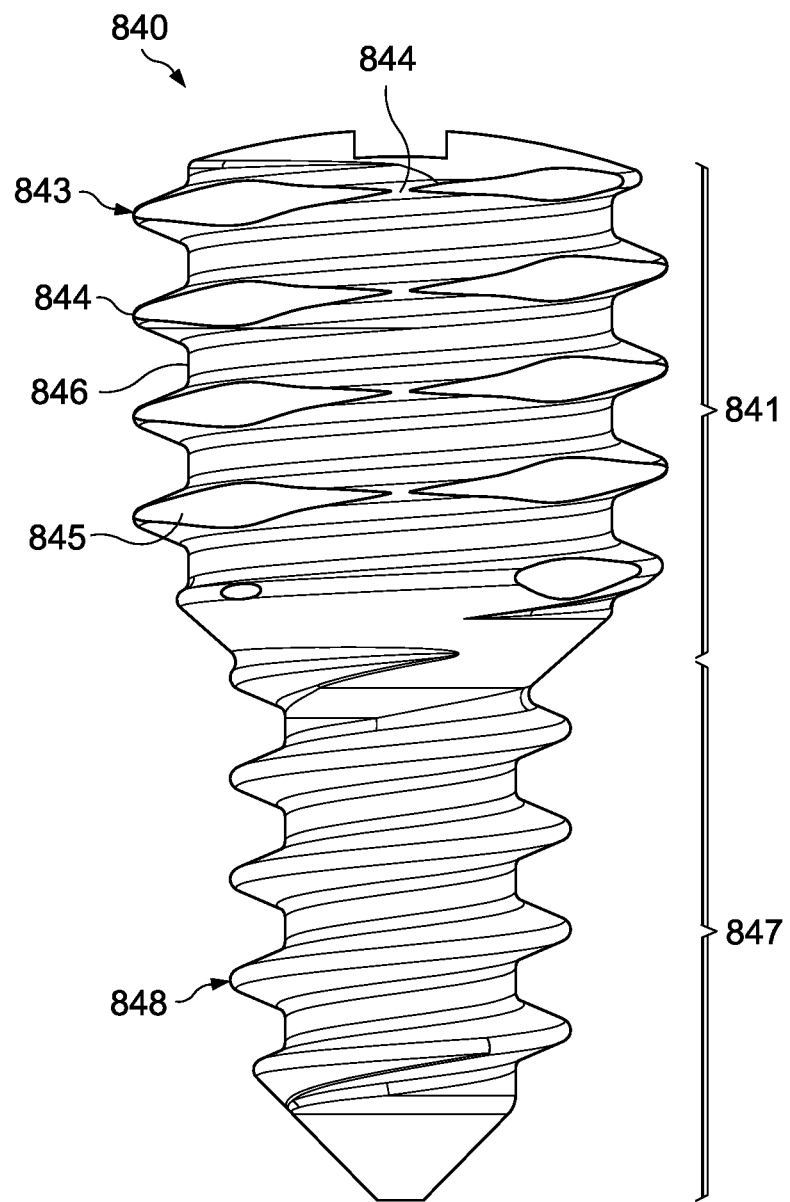
FIG. 8B illustrates a side view of the screw shown in FIG. 8A.
Figure 8C:
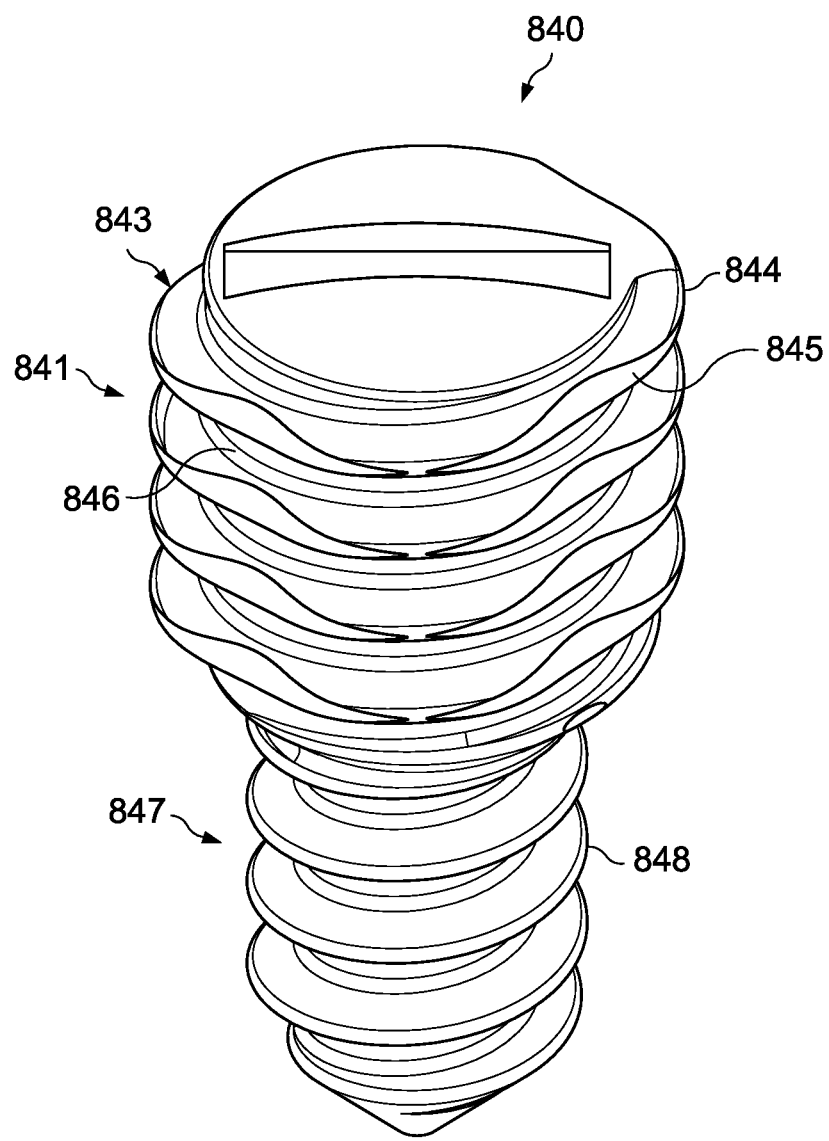
FIG. 8C illustrates a perspective view of the screw shown in FIG. 8A.

Specific example embodiments of a variable angle screw are illustrated in FIGS. 8A-8C. Variable angle screw 840 comprises head 841 and shank 847. As shown, head 841 has a generally cylindrical shape and comprises head thread 843 running from the upper end to the end that joins shank 847. Thread 843 comprises thread peak 844 and thread trough 846. Thread peak 844 has a radius ($r_{head}$) that varies along its length. Shank 847 has a generally cylindrical shape and comprises shank thread 848 encircling its length. The radius of shank thread 848 is substantially smaller than the head thread radius ($r_{head}$). In some embodiments, head thread 843 and shank thread 848 need not be distinct as shown. Head thread 843 comprises four sets of thread peaks 844 and indents 845 spaced apart at regular intervals. The minimum thread radius ($r_{head-min}$) is greater than the radius of the core of head 841. Thus, thread 843 is continuous in that it no point of zero thread height.

Figure 9:
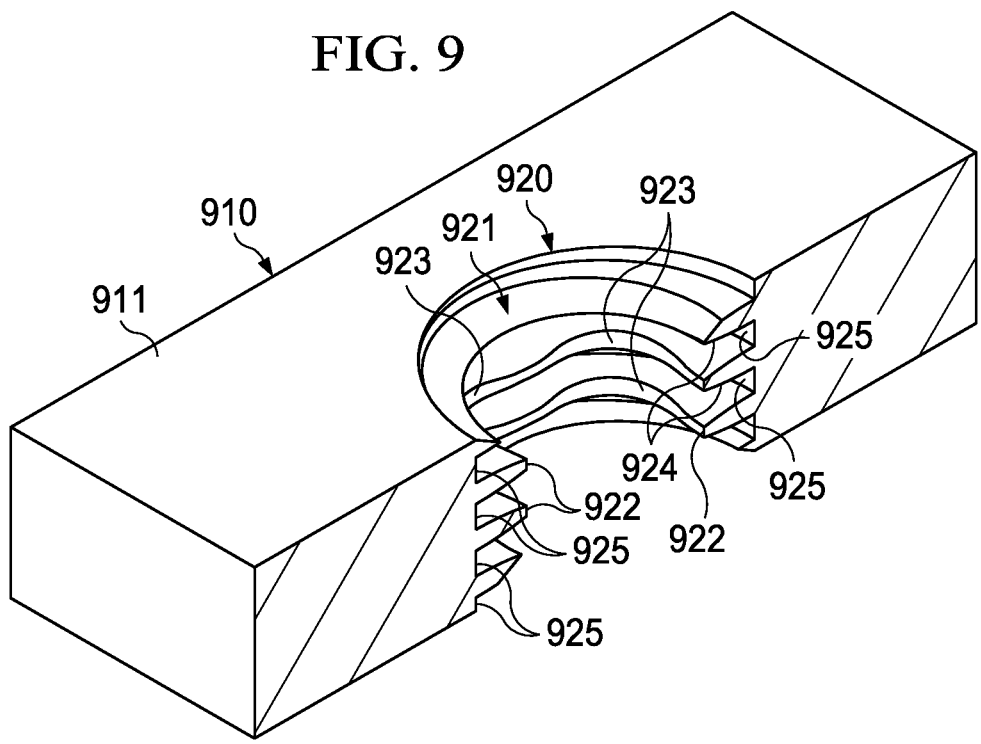
FIG. 9 illustrates a perspective view of a plate having a variable angle hole according to a specific example embodiment of the disclosure.

Specific example embodiments of a variable angle plate are illustrated in FIG. 9. Variable angle plate 910 comprises an upper surface 911, a lower surface 912, and at least one variable angle hole 920. Variable angle hole 920 has a generally cylindrical shape with continuous thread 921 and adjoining thread trough 925 around its circumference. Thread 921 comprises four sets of thread peaks 922 and indents 923 spaced apart at regular intervals. As shown, the upper-most turn of thread 921 has no indents.

Figure 10A:
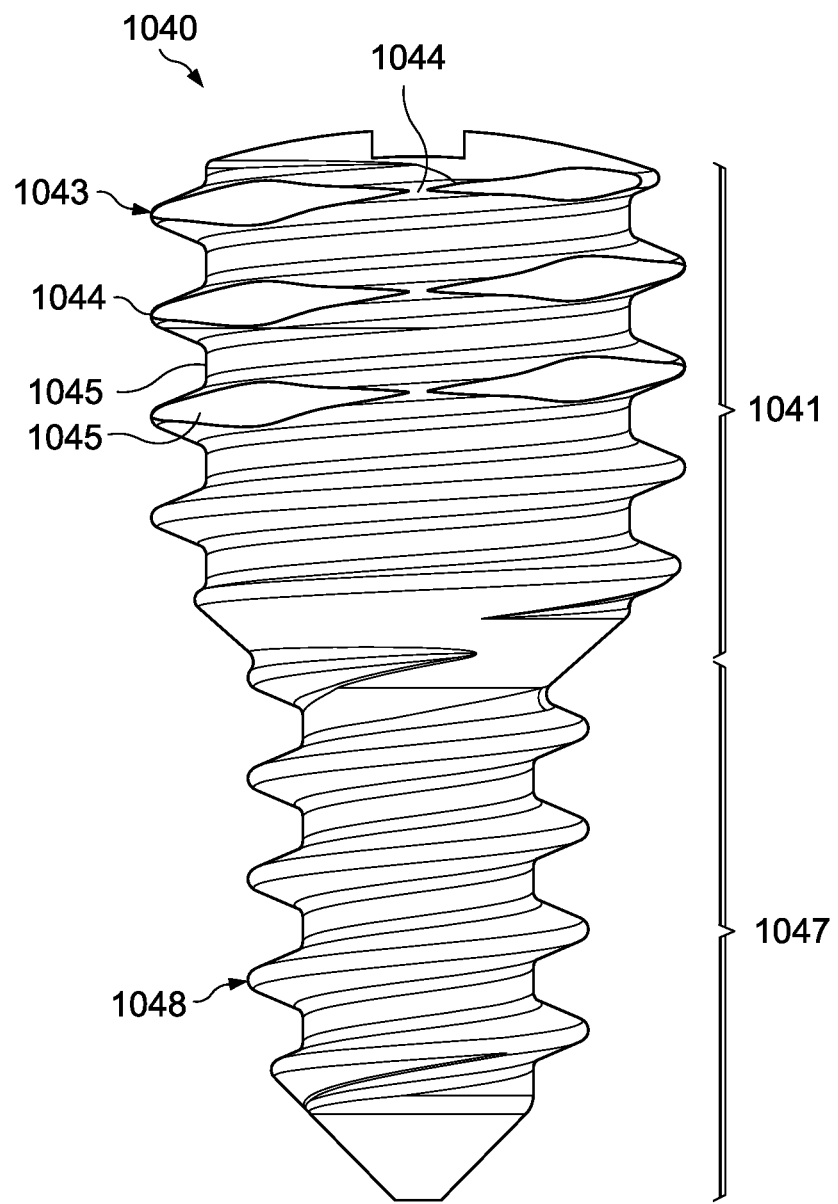
FIG. 10A illustrates a perspective view of a screw for insertion in a variable angle hole according to a specific example embodiment of the disclosure.
Figure 10B:
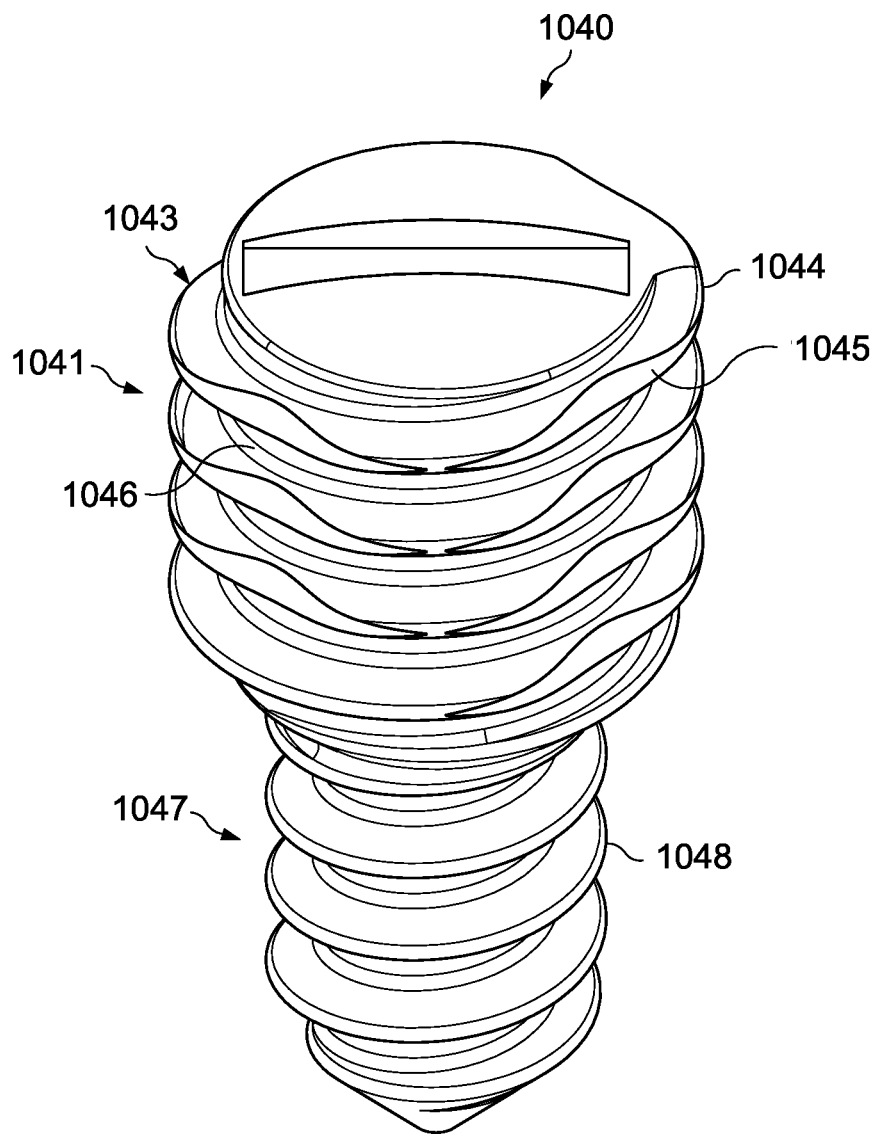
FIG. 10B illustrates a side view of the screw shown in FIG. 10A.

Specific example embodiments of a variable angle screw are illustrated in FIGS. 10A-10B. Variable angle screw 1040 comprises head 1041 and shank 1047. As shown, head 1041 has a generally cylindrical shape and comprises head thread 1043 running from the upper end to the end that joins shank 1047. Thread 1043 comprises thread peak 1044 and thread trough 1046. Head thread 1043 comprises four sets of thread peaks 844 and indents 845 spaced apart at regular intervals, except that the lower-most turn of thread 1043 has no indents.

As will be understood by those skilled in the art who have the benefit of the instant disclosure, other equivalent or alternative variable angle devices, system, and methods can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of fasteners, holes, threads, peaks, and/or indents may be varied. In some embodiments, variable angle bone plates, fixed angle bone plates, variable angle bone screws, fixed angle bone screws, and non-screw fasteners may be interchangeable. Interchangeability may allow fixation to be custom adjusted (e.g., by allowing the practitioner to use the most appropriate fastening means). In addition, the size of a device and/or system may be scaled up (e.g., to be used for adult subjects) or down (e.g., to be used for juvenile subjects) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. For example, a composition, device, and/or system may be prepared and or used as appropriate for animal and/or human use (e.g., with regard to sanitary, infectivity, safety, toxicity, biometric, and other considerations).

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/− about 10%, depicted value +/− about 50%, depicted value +/− about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for bone fixation may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

What is claimed is:

1. A variable angle orthopedic screw, the screw comprising:
   a threaded shank having an upper end and a tip; and
   a head fixed to the upper end of the shank, the head comprising:
   a generally cylindrical core of radius ($r_{core}$) and with a longitudinal axis,
   a single continuous thread encircling the core, the apex of which comprises a thread that defines an outer periphery of radius ($r_{head}$), wherein the radius ($r_{head}$) peak varies along the length of the thread; and
   a thread trough,
   wherein the thread has a plurality of indentations and a plurality of thread peaks, wherein the peaks and indentations are spaced apart at regular intervals along the length of the thread, each indentation having a radius ($r_{head-indent}$), wherein $r_{core} < r_{head-indent} < r_{head}$,
   wherein the thread has a minimum radius ($r_{head-min}$), wherein $r_{core} < r_{head-min}$, and
   wherein the variable angle screw is operable to engage a threaded hole of an orthopedic plate at a first angle aligned with the central hole axis and at least one other angle.

2. A variable angle orthopedic screw according to claim 1, wherein the at least one indentation further comprises a plurality of indentations arranged in at least one column parallel or substantially parallel to the longitudinal axis.

3. A variable angle orthopedic screw according to claim 2, wherein the at least one column further comprises 2 columns, 3 columns, 4 columns, 5 columns, or 6 columns, each parallel or substantially parallel to the longitudinal axis and spaced around the longitudinal axis.

4. A variable angle orthopedic screw according to claim 3, wherein spaced around the longitudinal axis further comprises spaced uniformly around the longitudinal axis.

5. A variable angle orthopedic screw according to claim 1, wherein the thread spans the length of the head.

6. A variable angle orthopedic screw according to claim 1, wherein the thread further comprises one or more turns around the circumference of the core.

7. A variable angle orthopedic screw according to claim 1, wherein $r_{core}$ is about 25% to about 98% $r_{head}$, and $r_{head-indent}$ is about 26% to about 99% $r_{head}$.

8. A variable angle orthopedic screw according to claim 1, wherein $r_{core}$ is about 25% to about 75% $r_{head}$, and $r_{head-indent}$ is about 26% to about 90% $r_{head}$.

9. A variable angle orthopedic screw, the screw comprising:
   a threaded shank; and
   a head fixed to the shank, the head comprising at least one thread spanning at least one turn around the circumference of the head, the apex of which comprises a thread peak that defines a thread height that varies along the length of the thread, each head thread turn comprising:
   a first region having a maximum thread height ($h_{max1}$),
   a second region having a maximum thread height ($h_{max2}$), a third region having a minimum thread height ($h_{min3}$) positioned between the first region and the second region, wherein $h_{max1}>h_{min3}$, $h_{max2}>h_{min3}$, and $h_{min3}>0$ for each turn independently, a fourth region having a maximum thread height ($h_{max4}$), and a fifth region having a minimum thread height ($h_{min5}$) positioned between the second region and the fourth region, wherein $h_{max2}>h_{min5}$, $h_{max4}>h_{min5}$, and $h_{min5}>0$ for each turn independently;

wherein the third regions of each turn are aligned in a column parallel or substantially parallel with the longitudinal axis of the screw; and wherein the fifth regions of each turn are aligned in a column parallel or substantially parallel with the longitudinal axis of the screw.

10. A variable angle orthopedic screw according to claim 9, wherein each turn further comprises:

a sixth region having a maximum thread height ($h_{max6}$), and a seventh region having a minimum thread height ($h_{min7}$) positioned between the fourth region and the sixth region, wherein $h_{max4}>h_{min7}$, $h_{max6}>h_{min7}$, and $h_{min7}>0$, wherein the seventh regions of each turn are aligned in a column parallel or substantially parallel with the longitudinal axis of the screw.

11. A variable angle orthopedic screw according to claim 10, wherein each turn further comprises:

an eighth region having a maximum thread height ($h_{max8}$), and a ninth region having a minimum thread height ($h_{min9}$) positioned between the sixth region and the eighth region, wherein $h_{max6}>h_{min9}$, $h_{max8}>h_{min9}$, and $h_{min9}>0$, wherein the ninth regions of each turn are aligned in a column parallel or substantially parallel with the longitudinal axis of the screw.

12. A variable angle orthopedic screw according to claim 11, wherein $h_{min3}\approx h_{min5}\approx h_{min7}\approx h_{min9}$.

13. A variable angle orthopedic screw according to claim 12, wherein $h_{max1}\approx h_{max2}\approx h_{max4}\approx h_{max6}\approx h_{max8}$.

14. A variable angle orthopedic screw according to claim 13, wherein minimum thread height ($h_{min3}$) is about 1% to about 80% of maximum thread height ($h_{max1}$).

15. A variable angle orthopedic screw according to claim 13, wherein minimum thread height ($h_{min3}$) is about 5% to about 60% of maximum thread height ($h_{max1}$).

16. A variable angle orthopedic screw according to claim 11, wherein $h_{max1}\approx h_{max2}\approx h_{max4}\approx h_{max6}\approx h_{max8}$.

17. A variable angle orthopedic screw according to claim 11, wherein the circumferential extent of the first region, the second region, the fourth region and the sixth region total more than 180°, the circumferential extent of the third region, the fifth region, and the seventh region total less than 180°, and circumferential extent of the first, second, third, fourth, fifth, sixth, and seventh regions total 360° or less.

18. A variable angle orthopedic screw according to claim 11, wherein the circumferential extent of the first region, the second region, the fourth region and the sixth region total more than 210°, the circumferential extent of the third region, the fifth region, and the seventh region total less than 150°, and circumferential extent of the first, second, third, fifth, sixth, and seventh regions total 360° or less.

19. A variable angle orthopedic screw according to claim 11, wherein the thread further comprises at least one of the following transitions from one region to the next region: step-wise transitions, graded transitions, and smooth transitions.

20. A variable angle orthopedic screw according to claim 9, wherein each thread minimum is from about 1% to about 90% of the adjacent thread maxima.

21. A variable angle orthopedic screw according to claim 9, wherein each thread minimum is from about 5% to about 80% of the adjacent thread maxima.

22. A variable angle orthopedic screw according to claim 21, wherein the at least two turns around the circumference of the head further comprises at least three turns around the circumference of the head.

23. A variable angle orthopedic screw according to claim 9, wherein the at least one thread spanning at least one turn around the circumference of the head further comprises at least two turns around the circumference of the head.

24. A variable angle orthopedic screw according to claim 9, wherein the head has a generally cylindrical shape.

25. A variable angle orthopedic screw, the screw comprising:

a variable angle head comprising at least one thread spanning at least a first turn and a second turn around the circumference of the head, wherein the apex of the thread comprises a thread peak that defines a thread height that varies along the length of the thread, wherein the first turn comprises:

a first region having a maximum thread height ($h_{max1-1}$), a second region having a maximum thread height ($h_{max1-2}$), and a third region having a minimum thread height ($h_{min1-3}$) positioned between the first region and the second region, wherein $h_{max1-1}>h_{min1-3}$, $h_{max1-2}>h_{min1-3}$, and $h_{min1-3}>0$, wherein the second turn comprises:

a first region having a maximum thread height ($h_{max2-1}$), a second region having a maximum thread height ($h_{max2-2}$), and a third region having a minimum thread height ($h_{min2-3}$) positioned between the first region and the second region, wherein $h_{max2-1}>h_{min2-3}$, $h_{max2-2}>h_{min2-3}$, and $h_{min2-3}>0$, wherein the third region of the first turn and the third region of the second turn are aligned in a column parallel or substantially parallel with the longitudinal axis of the head.

26. A variable angle orthopedic screw according to claim 25, wherein $h_{max1-1}\approx h_{max1-2}$.

27. A variable angle orthopedic screw according to claim 25, wherein minimum thread height ($h_{min1-3}$) is about 1% to about 80% of maximum thread height ($h_{max1-1}$).

* * * * *